US011864819B2

(12) United States Patent
Ineson

(10) Patent No.: US 11,864,819 B2
(45) Date of Patent: *Jan. 9, 2024

(54) ADJUSTABLE ELECTROSURGICAL PENCIL WITH SLIDABLE VENT TUBE

(71) Applicant: Covidien LP, Mansfield, MA (US)

(72) Inventor: Leonard Ineson, Mississauga (CA)

(73) Assignee: Covidien LP, Mansfield, MA (US)

( * ) Notice: Subject to any disclaimer, the term of this patent is extended or adjusted under 35 U.S.C. 154(b) by 248 days.

This patent is subject to a terminal disclaimer.

(21) Appl. No.: 17/317,219

(22) Filed: May 11, 2021

(65) Prior Publication Data
US 2021/0267662 A1 Sep. 2, 2021

Related U.S. Application Data

(63) Continuation of application No. 15/996,664, filed on Jun. 4, 2018, now Pat. No. 11,000,329, which is a (Continued)

(51) Int. Cl.
*A61B 18/14* (2006.01)
*A61B 18/00* (2006.01)

(52) U.S. Cl.
CPC .. *A61B 18/1402* (2013.01); *A61B 2018/0091* (2013.01); *A61B 2018/00172* (2013.01); (Continued)

(58) Field of Classification Search
CPC ...... A61B 2018/00178; A61B 18/1402; A61B 18/14; A61B 2018/1412;
(Continued)

(56) References Cited

U.S. PATENT DOCUMENTS 4,347,842 A 9/1982 Beale
4,562,838 A 1/1986 Walker
(Continued)

FOREIGN PATENT DOCUMENTS

WO 2012155922 A2 11/2012

OTHER PUBLICATIONS

Supplementary European Search Report dated May 2, 2016 in corresponding European Patent Application No. 12 88 3776, 7 pages.

(Continued)

*Primary Examiner* — Sean W Collins
(74) *Attorney, Agent, or Firm* — Carter, DeLuca & Farrell LLP

(57) ABSTRACT

An electrosurgical pencil for use in performing surgery on a surgical site includes a main body forming a handle grippable by user and having open front and rear ends. The pencil has a vent tube open at its forward end, and slidably mounted in the body. The tube is adjustable independently from a retracted position to various extended positions. An elongate electrode is mounted in the tube and independently slidable therein. The electrode is adjustable manually in its longitudinal direction from a retracted position to extended positions. A first conducting strip can be mounted in the vent rube in contact with the electrode. A second conducting strip can be mounted in the main body and is in sliding contact with the first strip in order to provide power to the electrode.

17 Claims, 16 Drawing Sheets

Related U.S. Application Data continuation of application No. 14/424,795, filed as application No. PCT/CA2013/000741 on Aug. 23, 2013, now Pat. No. 9,987,074.

(60) Provisional application No. 61/693,826, filed on Aug. 28, 2012.

(52) U.S. Cl.
CPC ........... *A61B 2018/00178* (2013.01); *A61B 2018/00184* (2013.01); *A61B 2018/00607* (2013.01); *A61B 2018/00916* (2013.01); *A61B 2018/00928* (2013.01); *A61B 2018/1412* (2013.01); *A61B 2018/1475* (2013.01); *A61B 2217/005* (2013.01); *A61B 2218/007* (2013.01); *A61B 2218/008* (2013.01)

(58) Field of Classification Search
CPC .... A61B 2018/1425; A61B 2018/1427; A61B 2018/1432; A61B 2018/1435; A61B 2018/144; A61B 2218/006; A61B 2218/007; A61B 2218/008
See application file for complete search history.

(56) References Cited

U.S. PATENT DOCUMENTS

| | | | |
|---|---|---|---|
| 4,683,884 | A | 8/1987 | Hatfield et al. |
| 4,719,914 | A | 1/1988 | Johnson |
| 4,850,352 | A | 7/1989 | Johnson |
| 4,911,159 | A | 3/1990 | Johnson et al. |
| 4,919,129 | A | 4/1990 | Weber, Jr. et al. |
| 5,013,300 | A | 5/1991 | Williams |
| 5,035,695 | A * | 7/1991 | Weber, Jr. .......... A61B 18/1402 606/49 |
| 5,071,418 | A | 12/1991 | Rosenbaum |
| 5,085,657 | A | 2/1992 | Ben-Simhon |
| 5,108,389 | A | 4/1992 | Cosmescu |
| 5,154,709 | A | 10/1992 | Johnson |
| 5,181,916 | A | 1/1993 | Reynolds et al. |
| 5,192,267 | A | 3/1993 | Shapira et al. |
| 5,197,963 | A | 3/1993 | Parins |
| 5,199,944 | A | 4/1993 | Cosmescu |
| 5,234,428 | A | 8/1993 | Kaufman |
| 5,242,442 | A | 9/1993 | Hirschfeld |
| 5,318,516 | A | 6/1994 | Cosmescu |
| 5,318,565 | A | 6/1994 | Kuriloff et al. |
| 5,348,555 | A | 9/1994 | Zinnanti |
| 5,360,427 | A | 11/1994 | Majlessi |
| 5,413,575 | A | 5/1995 | Haenggi |
| 5,431,650 | A | 7/1995 | Cosmescu |
| 5,449,357 | A | 9/1995 | Zinnanti |
| 5,451,222 | A | 9/1995 | De Maagd et al. |
| 5,451,223 | A | 9/1995 | Ben-Simhon |
| 5,460,602 | A | 10/1995 | Shapira |
| 5,479,019 | A | 12/1995 | Gross |
| 5,496,314 | A | 3/1996 | Eggers |
| D373,190 | S | 8/1996 | Monson |
| 5,554,172 | A | 9/1996 | Horner et al. |
| 5,578,000 | A | 11/1996 | Greff et al. |
| 5,593,406 | A | 1/1997 | Eggers et al. |
| 5,609,573 | A | 3/1997 | Sandock |
| D384,148 | S | 9/1997 | Monson |
| 5,674,219 | A | 10/1997 | Monson et al. |
| 5,681,262 | A | 10/1997 | Isse |
| 5,693,044 | A | 12/1997 | Cosmescu |
| 5,707,402 | A | 1/1998 | Heim |
| 5,797,901 | A | 8/1998 | Cosmescu |
| 5,800,431 | A | 9/1998 | Brown |
| 5,830,214 | A | 11/1998 | Flom et al. |
| 5,836,909 | A | 11/1998 | Cosmescu |
| 5,836,944 | A | 11/1998 | Cosmescu |
| 5,935,125 | A | 8/1999 | Zupkas |
| 5,951,548 | A | 9/1999 | DeSisto et al. |
| 5,968,042 | A | 10/1999 | Ernster |
| 6,099,525 | A | 8/2000 | Cosmescu |
| 6,120,498 | A | 9/2000 | Jani et al. |
| 6,142,995 | A | 11/2000 | Cosmescu |
| 6,149,648 | A | 11/2000 | Cosmescu |
| 6,210,323 | B1 | 4/2001 | Gilhuly et al. |
| 6,258,088 | B1 | 7/2001 | Tzonev et al. |
| 6,287,305 | B1 | 9/2001 | Heim et al. |
| 6,293,945 | B1 | 9/2001 | Parins et al. |
| 6,355,034 | B2 | 3/2002 | Cosmescu |
| 6,364,853 | B1 | 4/2002 | French et al. |
| 6,451,017 | B1 | 9/2002 | Moutafis et al. |
| 6,458,125 | B1 | 10/2002 | Cosmescu |
| 6,524,307 | B1 | 2/2003 | Palmerton et al. |
| 6,533,781 | B2 | 3/2003 | Heim et al. |
| 6,558,379 | B1 | 5/2003 | Batchelor et al. |
| 6,602,249 | B1 | 8/2003 | Stoddard et al. |
| 6,616,658 | B2 | 9/2003 | Ineson |
| 6,635,034 | B1 | 10/2003 | Cosmescu |
| 6,702,812 | B2 | 3/2004 | Cosmescu |
| 6,899,712 | B2 | 5/2005 | Moutafis et al. |
| 6,918,902 | B2 | 7/2005 | French et al. |
| 7,033,353 | B2 | 4/2006 | Stoddard et al. |
| 7,083,601 | B1 | 8/2006 | Cosmescu |
| 7,112,199 | B2 | 9/2006 | Cosmescu |
| 7,172,592 | B2 | 2/2007 | DeSisto |
| 7,303,559 | B2 | 12/2007 | Peng et al. |
| 7,329,253 | B2 | 2/2008 | Brounstein et al. |
| 7,377,919 | B2 | 5/2008 | Heim et al. |
| 7,537,594 | B2 | 5/2009 | Sartor |
| 7,731,713 | B2 | 6/2010 | Christoudias |
| 7,761,188 | B2 | 7/2010 | Palmerton et al. |
| 7,828,794 | B2 | 11/2010 | Sartor |
| 7,935,109 | B2 | 5/2011 | Cosmescu |
| 7,967,816 | B2 | 6/2011 | Ocel et al. |
| 8,057,470 | B2 | 11/2011 | Lee et al. |
| 8,095,241 | B2 | 1/2012 | Palmerton et al. |
| 8,109,929 | B2 | 2/2012 | Eitenmueller |
| 8,211,103 | B2 | 7/2012 | Greep |
| 8,414,576 | B2 | 4/2013 | Cosmescu |
| 8,518,018 | B2 | 8/2013 | Minskoff et al. |
| 8,690,872 | B2 | 4/2014 | Jayaraj |
| 8,702,700 | B2 | 4/2014 | Maeda et al. |
| 9,987,074 | B2 * | 6/2018 | Ineson ............... A61B 18/1402 |
| 11,000,329 | B2 * | 5/2021 | Ineson ............... A61B 18/1402 |
| 2002/0019631 | A1 | 2/2002 | Kidder et al. |
| 2002/0058931 | A1 | 5/2002 | Parker et al. |
| 2002/0072651 | A1 | 6/2002 | Vilos |
| 2002/0103485 | A1 | 8/2002 | Melnyk et al. |
| 2003/0088247 | A1 | 5/2003 | Ineson |
| 2004/0030328 | A1 | 2/2004 | Eggers et al. |
| 2004/0064136 | A1 | 4/2004 | Papineau et al. |
| 2004/0260280 | A1 | 12/2004 | Sartor |
| 2004/0267326 | A1 | 12/2004 | Ocel et al. |
| 2006/0058778 | A1 | 3/2006 | Arcusa Villacampa et al. |
| 2006/0264928 | A1 * | 11/2006 | Kornerup ........... A61B 18/1402 606/49 |
| 2007/0066970 | A1 | 3/2007 | Ineson |
| 2007/0129722 | A1 | 6/2007 | Cosmescu |
| 2007/0249990 | A1 | 10/2007 | Cosmescu |
| 2008/0103431 | A1 | 5/2008 | Brounstein et al. |
| 2008/0287893 | A1 | 11/2008 | Ineson |
| 2009/0018490 | A1 | 1/2009 | Wuchinich |
| 2009/0062791 | A1 * | 3/2009 | Lee .................... A61B 18/1402 606/45 |
| 2009/0076486 | A1 | 3/2009 | Cucin |
| 2009/0192441 | A1 | 7/2009 | Gelbart et al. |
| 2010/0094283 | A1 | 4/2010 | Cosmescu |
| 2010/0125172 | A1 | 5/2010 | Jayaraj |
| 2010/0168745 | A1 | 7/2010 | Loeser |
| 2011/0034921 | A1 | 2/2011 | Sartor |
| 2011/0077645 | A1 | 3/2011 | Lin |
| 2011/0190768 | A1 | 8/2011 | Shvetsov et al. |
| 2011/0230878 | A1 | 9/2011 | Ryan et al. |
| 2011/0319892 | A1 | 12/2011 | Blomeyer |
| 2012/0101497 | A1 | 4/2012 | Jayaraj |
| 2012/0203223 | A1 | 8/2012 | Terry et al. |
| 2012/0283718 | A1 | 11/2012 | Cosmescu |
| 2012/0283728 | A1 | 11/2012 | Cosmescu |

(56) References Cited

U.S. PATENT DOCUMENTS

2013/0006236 A1    1/2013  Greep et al.
2013/0204246 A1    8/2013  Greep et al.
2014/0046413 A1*   2/2014  Kane .................... A61N 1/0558
                                                            607/116
2014/0081086 A1    3/2014  Shvetsov et al.
2015/0005761 A1    1/2015  Zinnanti

OTHER PUBLICATIONS

Supplementary European Search Report dated May 18, 2016 in corresponding European Patent Application No. 13 83 2406.6, 7 pages.
Australian Examination Report No. 1, dated Apr. 19, 2017, corresponding to Australian Application No. 2013308032; 3 pages.
Australian Examination Report No. 1, dated May 17, 2017, corresponding to Australian Application No. 2012388657; 4 pages.
Australian Examination Report No. 1, dated May 23, 2018, corresponding to Australian Application No. 2014324006; 3 pages.
Canadian Office Action and Examination Search Report dated Sep. 28, 2018, corresponding to Canadian Application No. 2,883,231; 5 total pages.
Canadian Office Action dated Oct. 2, 2020, issued in corresponding Canadian Appln. No. 2,883,231, 4 pages.
Canadian Office Action dated Jul. 8, 2021, issued in corresponding Canadian Appln. No. 2,883,231, 4 pages.

* cited by examiner

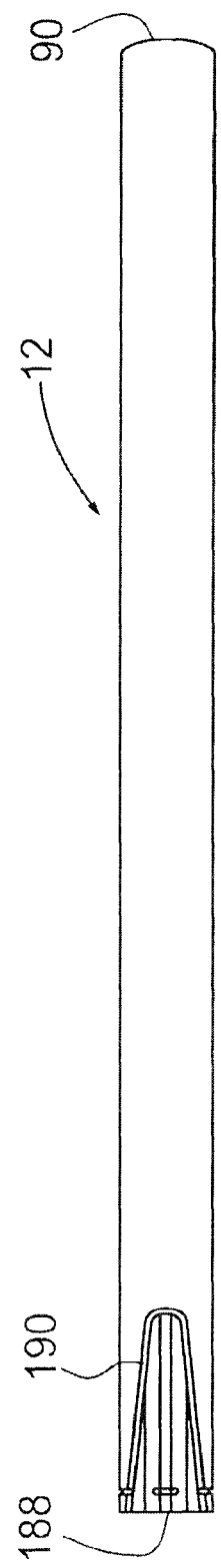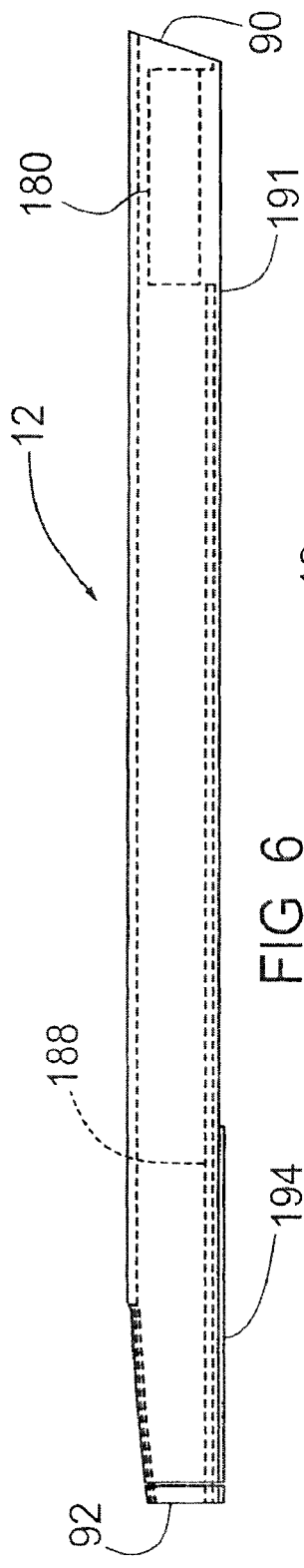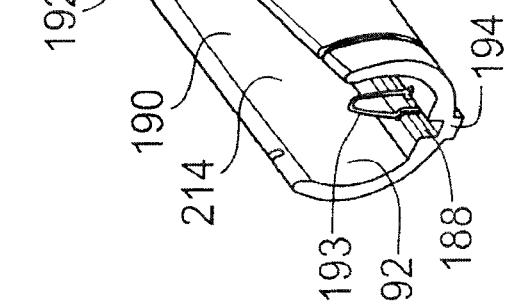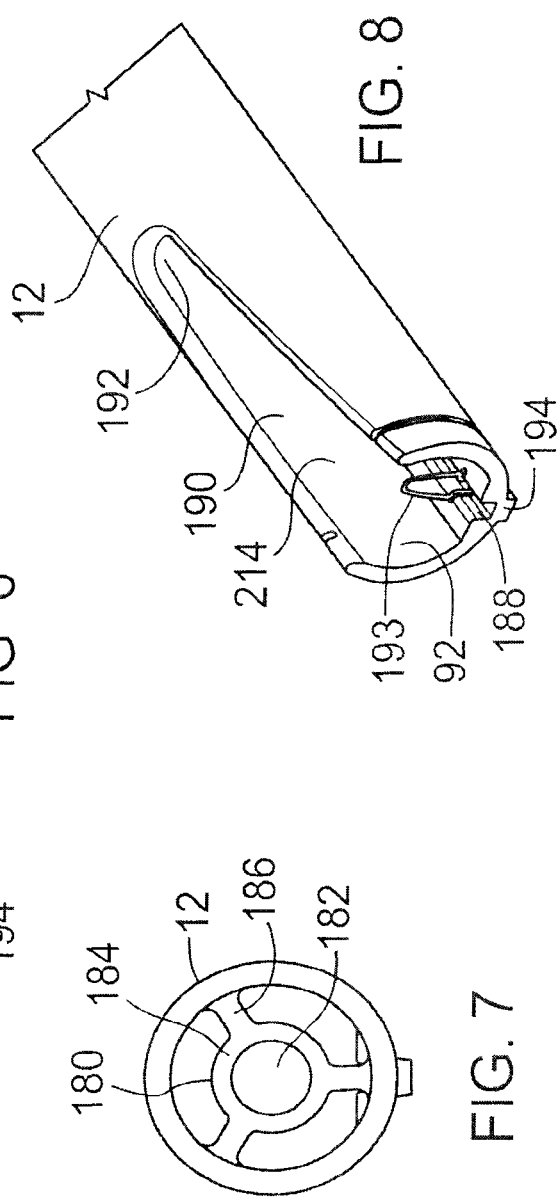

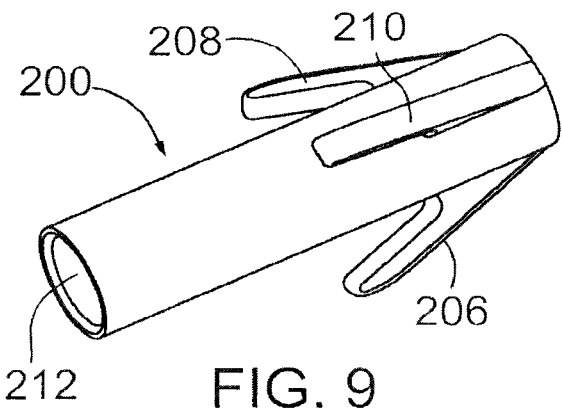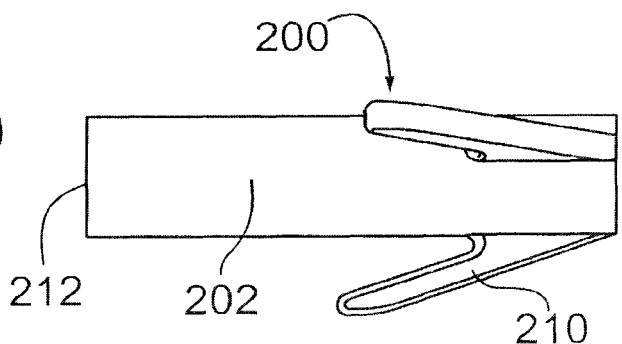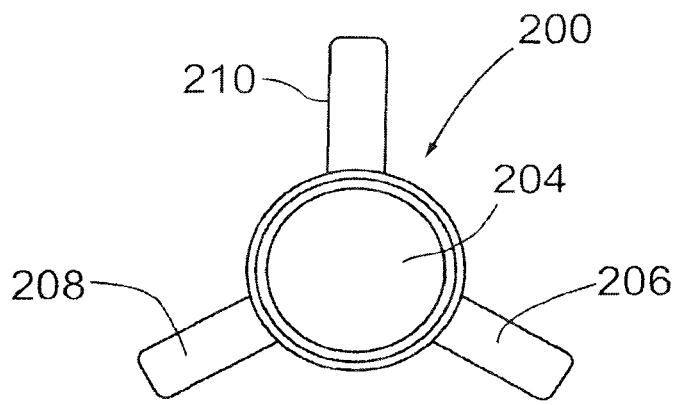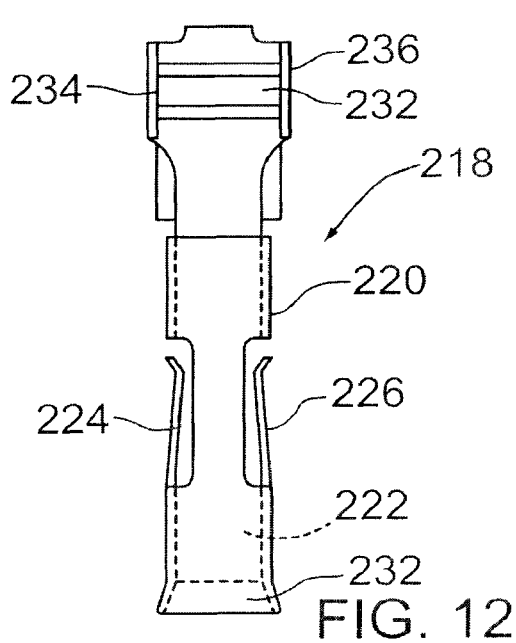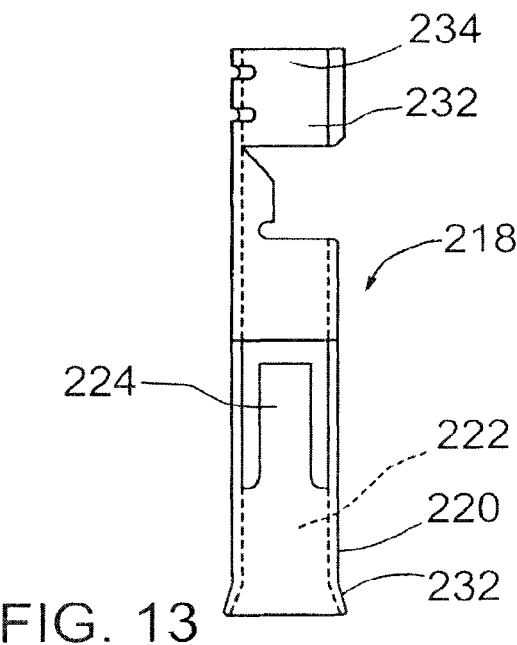

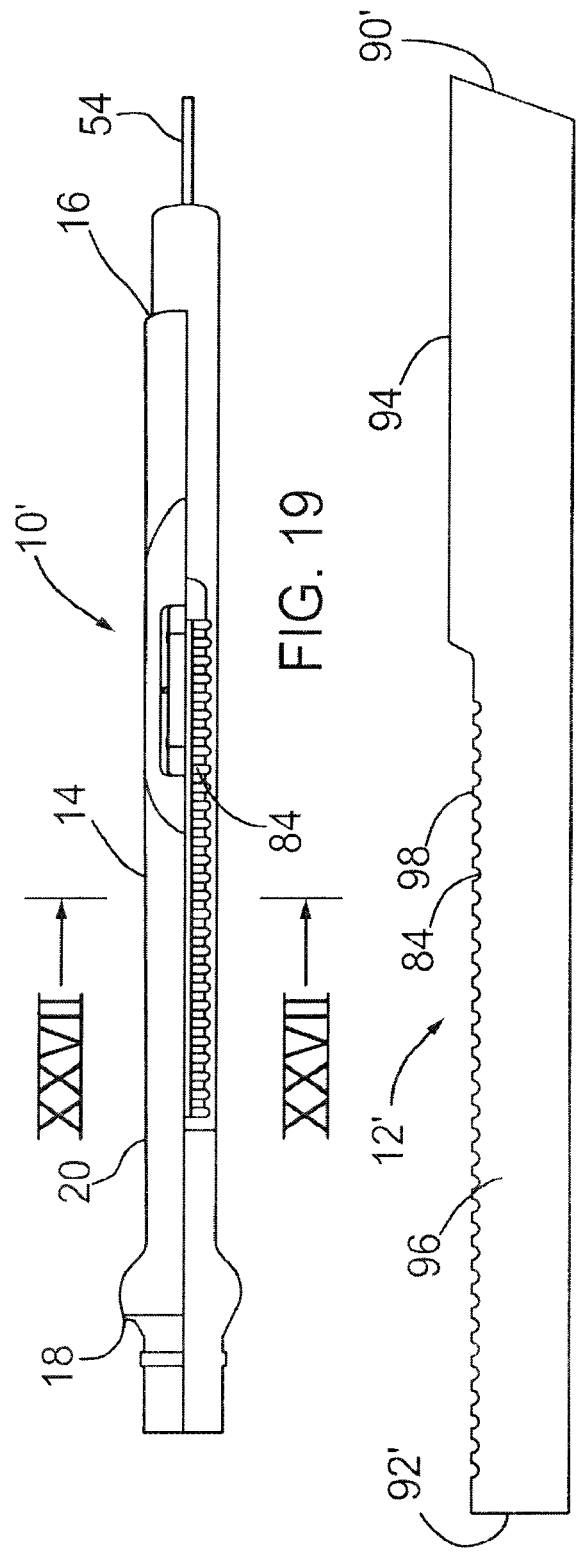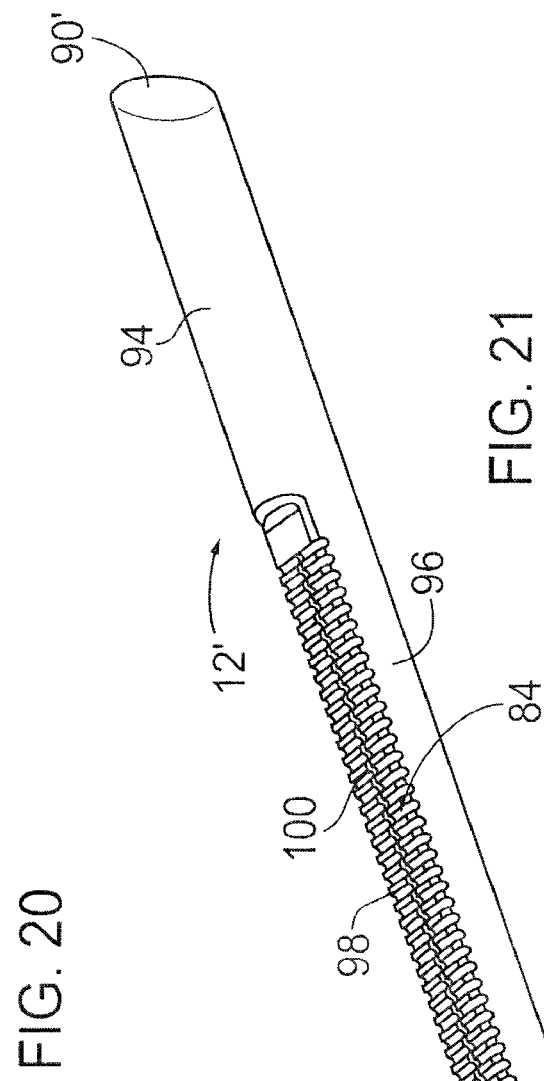

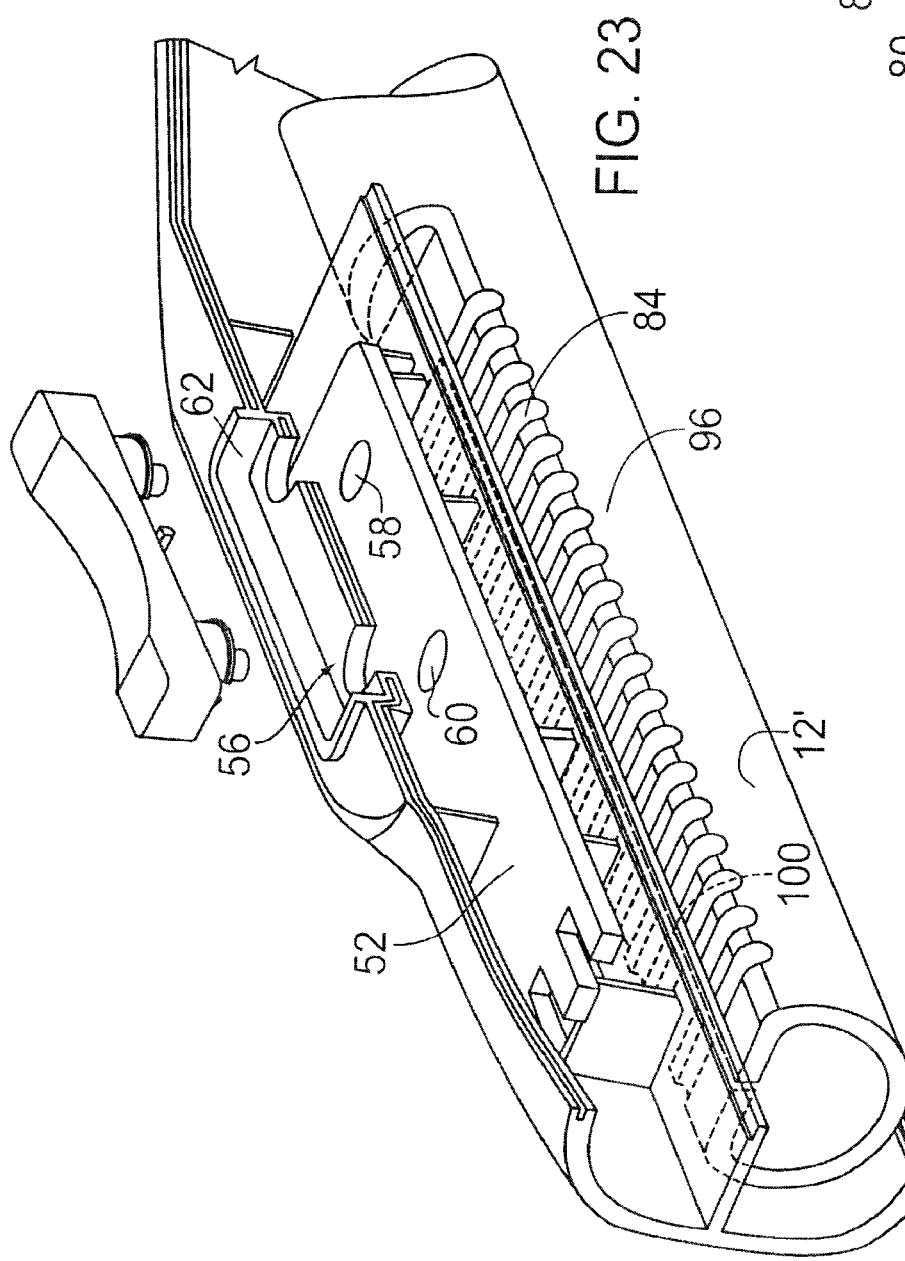
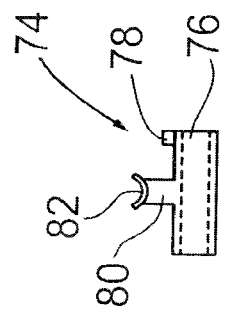
FIG. 23
FIG. 24

ADJUSTABLE ELECTROSURGICAL PENCIL WITH SLIDABLE VENT TUBE

CROSS-REFERENCE TO RELATED APPLICATIONS

This application is a continuation application of U.S. patent application Ser. No. 15/996,664, filed on Jun. 4, 2018, which is a continuation application of U.S. patent application Ser. No. 14/424,795, filed on Feb. 27 (now U.S. Pat. No. 9,987,074), 2015, which is a national stage entry of PCT/CA2013/000741, filed on Aug. 23, 2013, which claims the benefit of and priority to U.S. Provisional Patent Application No. 61/693,826, filed on Aug. 28, 2012. U.S. patent application Ser. No. 14/424,795 also claims foreign priority to Canada PCT CA2012/001200, filed on Dec. 21, 2012. The entire disclosures of all of the foregoing applications are incorporated by reference herein.

BACKGROUND

Technical Field

The present application relates to electrosurgical instruments and more particularly to electrical surgical pencils for cauterizing tissue and evacuating smoke from a surgical site.

Background of Related Art

The coagulation of blood vessels is a necessary part of medical surgery and can be performed by an electrosurgical tool commonly known as an electrosurgical pencil or coagulator pencil. In this type of pencil, an electrically conductive metal tip either in the form of a blade or a needle extends outwardly from the forward end of the body of the pencil, the latter acting as a hand grip for a surgeon using the pencil. In use, the tissue of a patient is electrically connected to one side of an electrosurgical circuit, and the electrically conductive tip is connected to the other side of this circuit. When the metal tip touches or is near the tissue at the surgical site, a high frequency electrical current flows from the electrode to the tissue, thus coagulating and cauterizing the tissue. Use of the aforementioned electrosurgical pencil produces small plumes of smoke which should be removed from the site. This smoke is offensive because of its odor and it is potentially dangerous to medical personnel. Also evacuation of the smoke is very desirable so that the surgeon's view of the operation site remains relatively unobscured.

Recent U.S. Pat. No. 6,616,658 which issued to the present applicant describes an electrosurgical pencil of the aforementioned type. This known pencil has a main body portion forming a handle grippable by a user and having an electrode end and an exhaust end. This pencil comes with a metal electrode tip having a plastic base and removably mounted in the main body portion. There is an electrical switch in the form of a double-throw rocker switch mounted on a small circuit board that is in turn mounted within a passage formed in the main body. An elongate substantial unobstructed airflow vent is disposed within the body portion so as to extend from the electrode end to the exhaust end thereof.

More recent U.S. Pat. No. 7,537,594 to J. D. Sartor describes an electrosurgical suction coagulator that includes a handle and an elongate tube electrode or conductive suction tube extending from a front end of the handle. The suction tube has a closed distal end and an elongate slot disposed therealong for slidably receiving a needle electrode which is selectively extendable relative to the closed distal end to facilitate precise dissection. An aspiration port is disposed along a side of the suction tube for removing surgical fluids. In one version of this known coagulator the suction tube is slidingly and rotatably received within a channel formed in the handle of the device. A control rod is mechanically coupled to the suction tube and can be manipulated by the user to extend, retract and/or rotate the suction tube. The user can also manipulate the needle electrode via another control rod which operates in a similar manner.

The electrosurgical pencil described herein has both an elongate vent tube which can be readily adjusted in its longitudinal direction manually by the surgeon and also an elongate electrode tool which is adjustable independently in its longitudinal direction by manually pulling on a projecting forward section of the electrode tool.

SUMMARY

In accordance with one aspect of the present application, an electrosurgical tool for use in performing surgery on a surgical site includes a main body forming a handle for a user and having a first end forming a front opening and an opposite second end forming an exhaust opening. The main body defines an airflow vent extending from the first end to the second end, the latter end being connectable for fluid communication via a flexible tubing to a suction source in order to permit evacuation of surgical smoke and debris. An elongate vent tube is mounted in the airflow vent and slidable therein. The position of this tube is adjustable in its longitudinal direction from a retracted position to a selected one of a plurality of extended positions where a forward end of the vent tube is located forwards of the first end of the main body. There is also an elongate electrode suitable for performing electrosurgery mounted in the vent tube and independently slidable therein. The position of this electrode is adjustable in its longitudinal direction between a retracted position and a selected one of a plurality of extended positions where a forward section of the electrode projects forwards from both the first end of the main body and the forward end of the vent tube. The tool includes an electrical switch for the tool connectable to an electrical control for the tool. The tool is characterized in that the electrical switch is mounted on the body portion, the position of the electrode is adjustable by pulling on a projecting forward section of the electrode, and the vent tube is open at its forward end. A first metal conducting strip is mounted in the vent tube and is in electrical contact with the electrode in any of the plurality of extended positions. A second metal conducting strip is mounted in the main body and adjacent to the vent tube. The two metal conducting strips are in sliding electrical contact with one another. The second conducting strip is adapted to electrically connect the first conducting strip to the electrical control.

In an exemplary version of this electrosurgical tool, a metal connector is mounted on a rear section of the electrode and a bent metal conducting tongue extends from the metal connector to the first metal conducting strip to provide an electrical connection that is slidable along the first conducting strip.

According to another aspect of the present application, an electrosurgical tool for use with a power source and a suction source includes an elongate body forming a handle for a user and an airflow vent extending from an open first end to an open second end which is connectable during use of the tool to the suction source. An elongate vent tube having a front end and rear end section open to the airflow vent is slidably mounted in the airflow vent for longitudinal movement. The position of the vent tube is adjustable longitudinally relative to the body. The vent tube has a front end section which projects forwardly from the first end of the body by an amount which is adjustable by a user of the tool. There is also provided an elongate electrode for performing surgery mounted in the vent tube and movable longitudinally relative to both the vent tube and the body. The electrode in use has a forward section projecting from the front end of the vent tube and is connected to the power source. An electrical circuit board is provided to control electrical operation of the electrode and is mounted in the body and connectable to the power source. The circuit board has a metal electrical connector mounted at one end of the board. A metal conducting strip is mounted in the elongate body and has a bent end section electrically connected to the metal connector. An elongate metal conducting member is mounted in the vent tube as is in sliding contact both with the electrode and the metal conducting strip.

In an exemplary version of this tool, the vent tube is formed internally with two longitudinal, spaced-apart rib-like connectors for the metal conducting member which is another conducting strip. These rib-like connectors extend at least a major portion of the length of the vent tube.

In a still further embodiment of the present application, an electrosurgical tool for use with an electrical power source and a suction source includes a body forming a handle for a user and an airflow vent extending rearwardly from an open front end of the body and having an outlet connectable to the suction source. The tool has an elongate vent tube for evacuating smoke or debris from a surgical site, this tube having a front end and outlet opening into the airflow vent. The vent tube is slidably mounted in the airflow vent for longitudinal movement and has a front section projecting forwards from the front end of the body. The length of the front section is manually adjustable by a user of the tool. An elongate electrode device for performing a surgical operation is mounted in the vent tube and slidable therein in the longitudinal direction relative to both the vent tube and the body. The electrode device in use projects from the front end of the vent tube and is operatively connected to the power source. This electrosurgical tool is characterized in that the front end of the vent tube is open and a separate metal connector is mounted on a rear section of the electrical device and has a bent metal conducting tongue extending from an end thereof. An elongate metal conducting member is mounted within the vent tube and extends longitudinally therein. The bent tongue slidingly engages the elongate conducting member. A further elongate metal conductor operatively engages the metal conducting member and is adapted to provide an electrical connection between the electrical conducting member and the power source. The tool also has a slide restricting mechanism for limiting sliding movement of the electrode device in a longitudinal direction relative to the vent tube and the body. The slide restricting mechanism acts to restrict movement of the electrode device unless sufficient force is applied to the vent tube in the longitudinal direction.

In a particular embodiment, the slide restricting mechanism is an electrode support member mounted on a rear section of the electrode and slidable therewith. This support member has radially projecting arms which engage an interior surface of the vent tube in a manner causing a friction fit.

Other advantages, features and characteristics of the present electrosurgical pencil will become apparent upon consideration of the following detailed description and the accompanying drawings.

BRIEF DESCRIPTION OF THE DRAWINGS

Reference will now be made, by way of example, to the accompanying drawings which show sample embodiments of the present application, and in which:

FIG. 5 is a top view of the vent tube of FIG. 4 shown separately;

FIG. 6 is a side view of the vent tube showing interior details in dash lines;

FIG. 7 is a front end view of the vent tube of FIG. 6;

FIG. 8 is a detail perspective view of a rear section of the vent tube, this view being taken from above and from the rear of the tube;

FIG. 9 is a perspective view of a tubular support member mounted at the rear end of the electrode;

FIG. 10 is a side view of the support member of FIG. 9;

FIG. 11 is a front end view of the support member of FIG. 9;

FIG. 12 is a first side view of a first version of a metal connector for attaching a wire to the electrode;

FIG. 13 is a second side view of the metal connector as seen from the right side of FIG. 12;

FIG. 19 is a partial cross section of another embodiment of an electrosurgical pencil according to the application with the right half of the pencil (bottom half as viewed in FIG. 19) shown in cross section to show internal features FIG. 20 is a longitudinal side view of the vent tube used in the pencil of FIG. 19;

FIG. 21 is a perspective view of the vent tube shown in FIG. 20, this view being taken from above and from the rear end;

FIG. 23 is a perspective view partly in vertical cross section illustrating one form of mounting of a first version of the circuit board and switch in the main body of the pencil;

FIG. 24 is a detail side view of a spring clip attachment that connects to the rear end of the electrode blade in the embodiment of FIG. 19;

DETAILED DESCRIPTION

Figure 1:
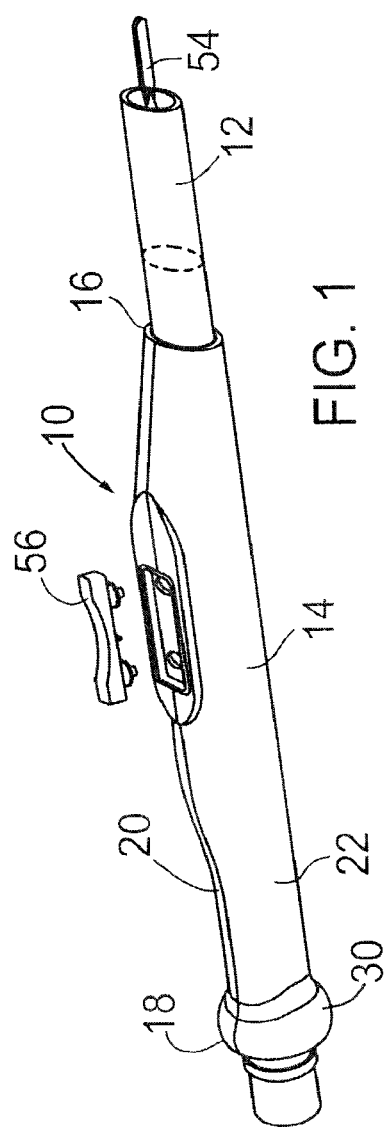
FIG. 1 is a perspective view of a first embodiment of electrosurgical pencil constructed according to the present application, this view being taken from above and from the right side.
Figure 2:
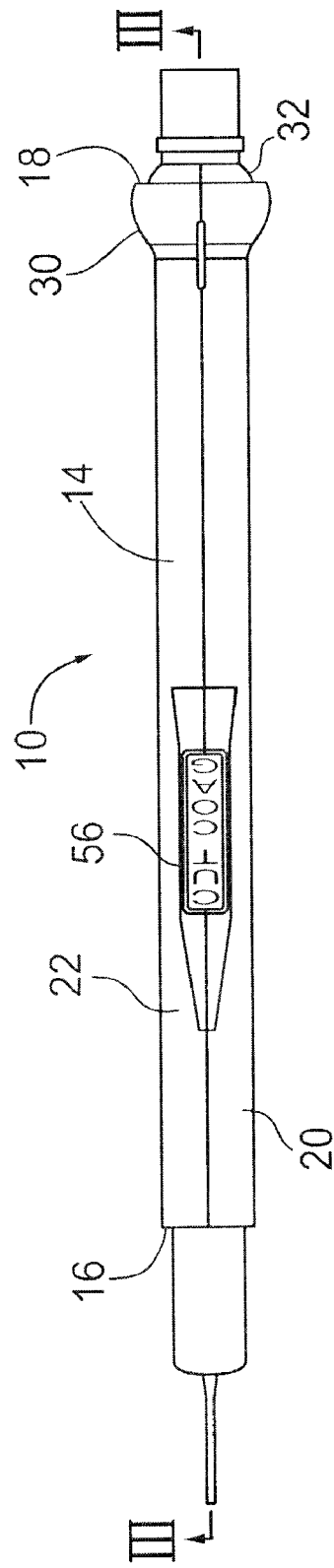
FIG. 2 is a top view of the electrosurgical pencil.

FIGS. 1 to 4 illustrate a first embodiment of an electrosurgical pencil 10 constructed in accordance with the application. FIGS. 5 to 8 illustrate an elongate vent tube 12 for use in the pencil 10. The electrosurgical pencil 10 is for use in performing surgery on a surgical site, this pencil including a main body portion 14 forming a handle grippable by a user, for example a surgeon. The main body portion is shaped for ease of comfort by the user. The body portion 14 includes an open electrode end 16 and an open exhaust end 18. The main body portion is made from a suitable plastic material, such as polyethylene, and it can be constructed from two half sections 20,22 that extend the length of the main body portion. These half sections can be rigidly and permanently attached to each other by such known methods as ultrasonic welding or adhesive bonding. It should be noted that the pencil 10 is intended for one time use only and is disposed of after surgery.

Figure 4:
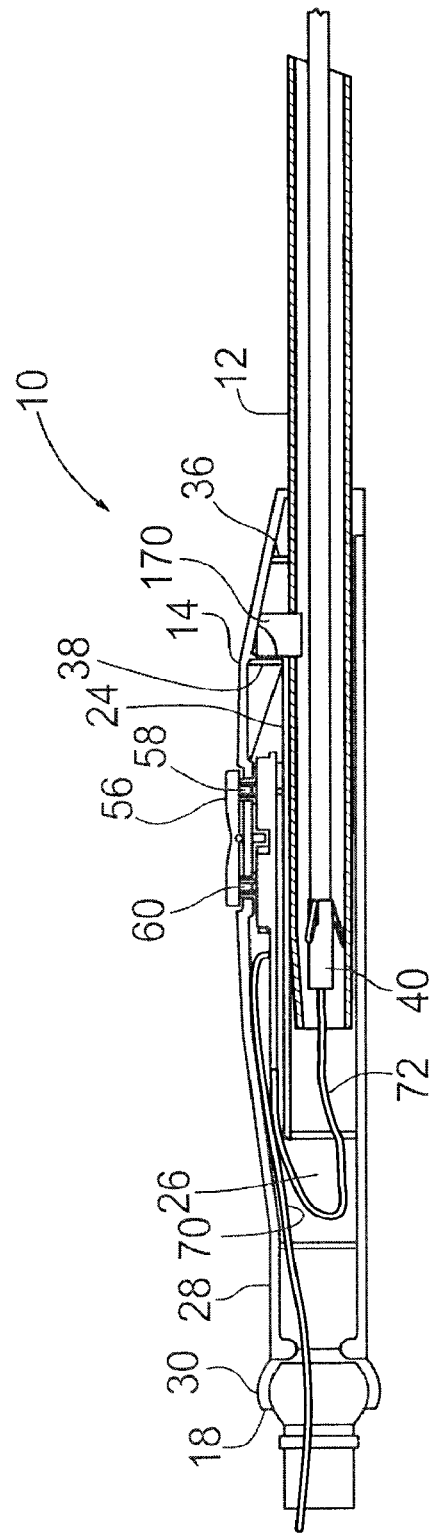
FIG. 4 is a longitudinal cross-section similar to FIG. 3 but showing the vent tube in cross-section.

The main body portion has an internal longitudinal wall structure 24 that together with outer walls of the half sections 20,22 form an elongate airflow vent 26 extending from the electrode end 16 to the exhaust end 18. As illustrated in FIG. 4, the vent 26 has a wider section 28 adjacent to the exhaust end and this section includes a rounded ball socket 30 which receives a separate ball-swivel member 32 shown in greater detail in FIG. 16.

Figure 14:
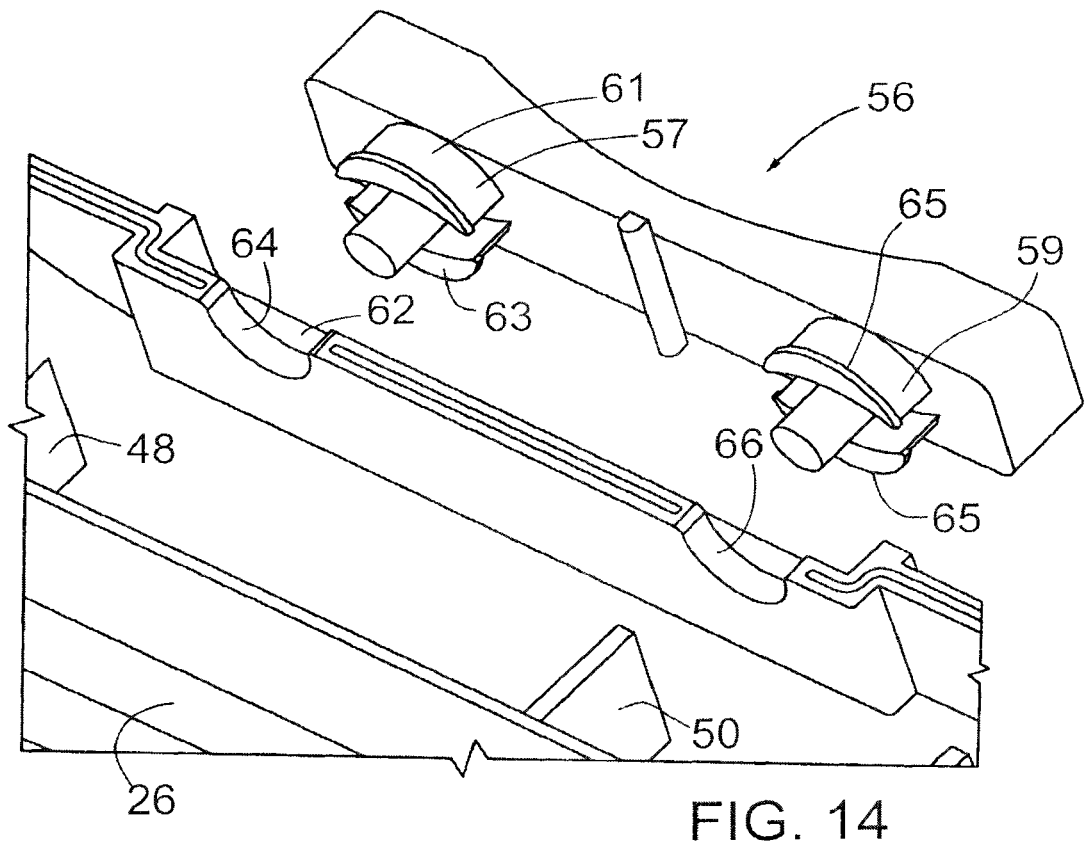
FIG. 14 is a detail perspective view of one-half of the inside of the main body of the pencil, this view showing the region where the circuit board and electrical switch are mounted.
Figure 15:
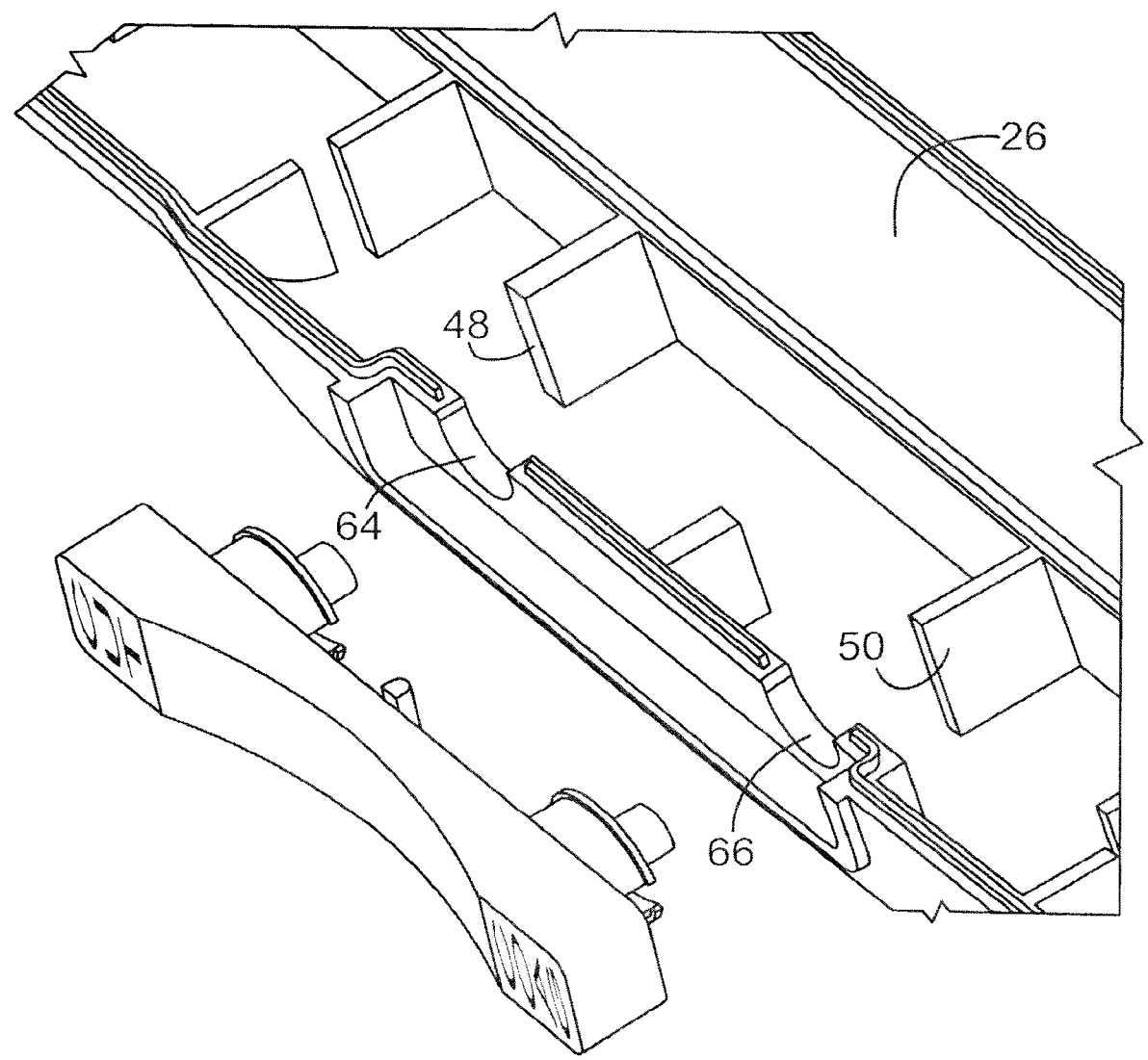
FIG. 15 is another detail perspective view of one-half of the inside of the main body portion of the pencil showing the region where the circuit board and switch are mounted.

The main body portion includes transverse support walls 36,38,40 viewable in FIG. 4 plus a couple of short transverse walls 48,50 visible in FIGS. 14 and 15. The short transverse walls 48,50 support a circuit board 52 illustrated in FIGS. 3, 4 and 23. In an alternate construction, the walls 48, 50 can be omitted. The circuit board is for regulating and controlling electrical operation of an elongate, heatable electrode tool 54 which either can be in the form of a scalpel or blade (as shown) or a needle. An electrical switch mechanism 56 is mounted on the main body portion 14 so as to be operable externally on the main body portion and the circuit board is operated by this switch mechanism. The switch 56 can be a rocker switch similar to that used in applicant's prior U.S. Pat. No. 6,616,658. The switch 56 is a single-pole, double-throw rocker type electrical switch mounted on top of the body portion and above the circuit board 52. The illustrated switch has two downwardly projecting pins 58, 60 which project through two holes in a recessed section 62 of the main body portion. Round holes 64, 66 are formed near opposite ends of the recessed section 62. Only one-half of each of these holes is shown in FIGS. 14 and 15. In use, the forward end of the switch can be pressed by the surgeon to provide a higher frequency signal to the electrode tool 54 for cutting tissue and the rearward end of the switch 56 is pressed to provide a lower frequency signal to the electrode tool for cauterizing tissue. The switch shown in FIG. 2 has molded lettering CUT and COAG formed thereon to clearly indicate these two switch functions.

Figure 3:
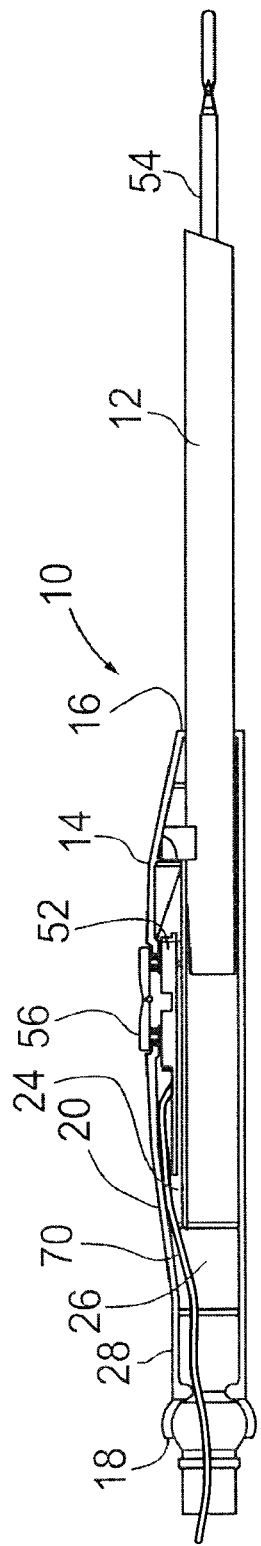
FIG. 3 is a longitudinal vertical cross-section of the pencil taken along the line of FIG. 2 with the vent tube not in cross-section.
Figure 22:
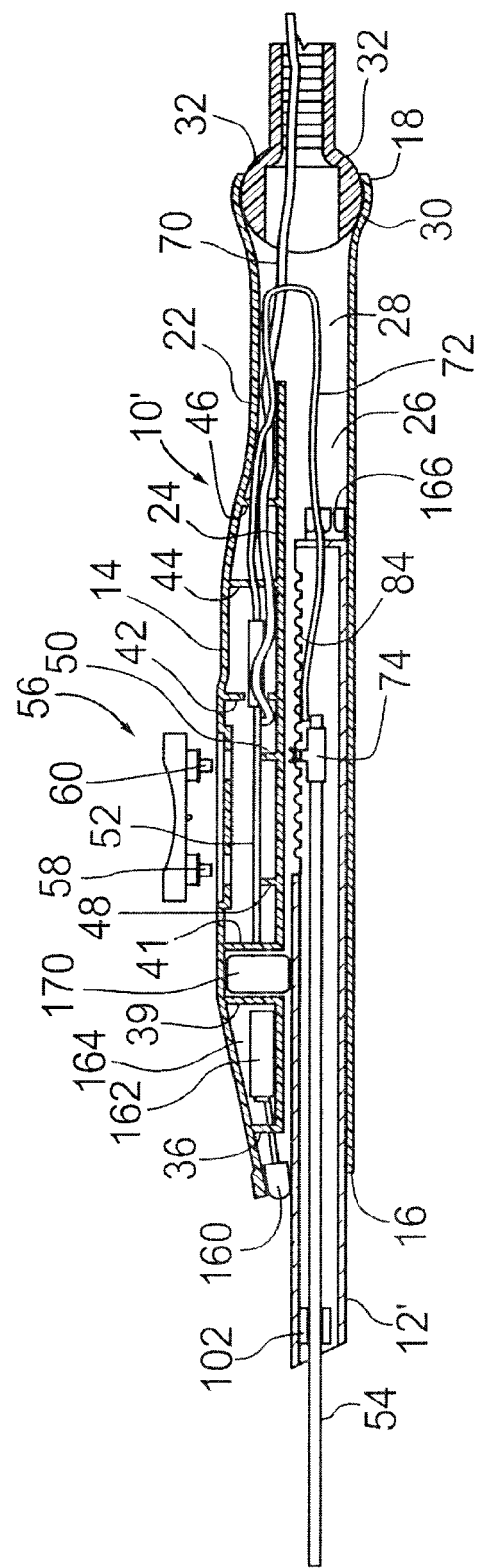
FIG. 22 is a longitudinal cross section of the second embodiment taken along the line XXII-XXII of FIG. 19.
Figure 25:
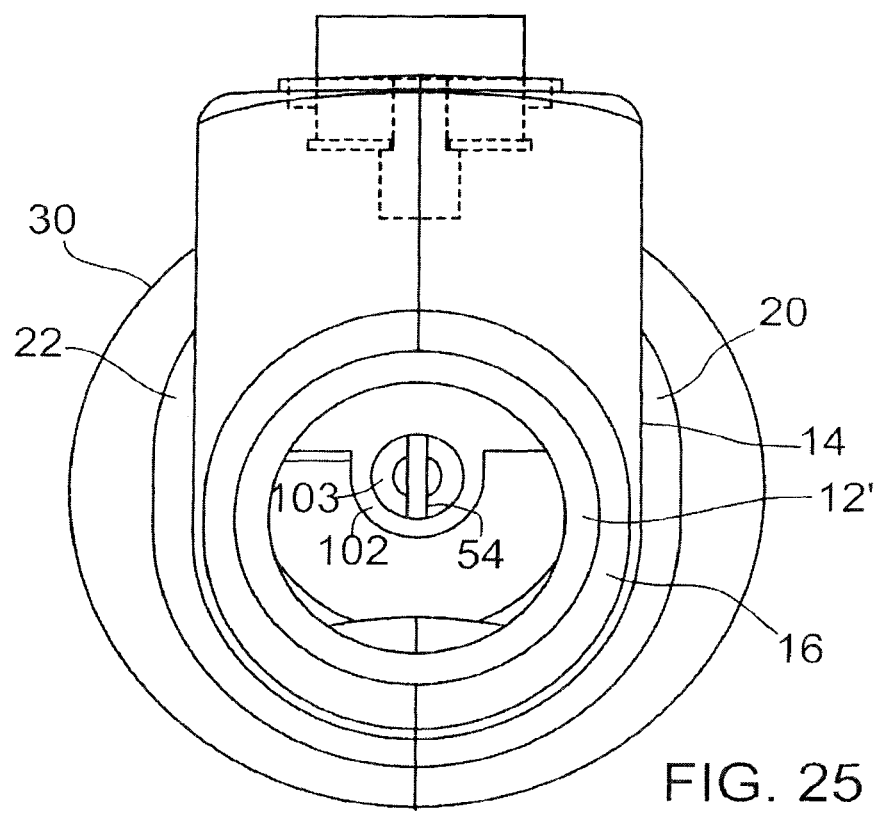
FIG. 25 is a front end view of the pencil of FIG. 19.

In the first embodiment of the pencil as illustrated in FIGS. 3 and 22, an insulated wire 70 enters an upper section of the main body portion through the ball-swivel member 32 and is connected to the circuit board 52. The wire is electrically connected to one of the terminals operated by the electrical switch mechanism while another terminal is connected electrically to the electrode tool by means of a second insulated wire 72 shown in FIGS. 4 and 22. The wire 72 is relatively thin so that it is highly flexible and bendable during use of the pencil.

FIGS. 5 to 8 illustrate a first embodiment of vent tube 12 which is preferably made of transparent plastic and has an open front end 90 and an open rear end at 92. If desired, the front end can be cut or formed at an acute angle to the longitudinal axis of the tube. Smoke form a surgical site can pass through the entire length of this vent tube. Except for a short rear end section, the tube has a circular transverse cross-section. Located at or near the front end of the tube is an eyelet guide 180 having a circular passage 182 through which the electrode tool extends as illustrated in FIG. 4. The passage is formed by a cylindrical section 184 which is coaxial with the central longitudinal axis of the tube. Projecting radially outwardly from the cylindrical section are integral connecting webs 186. The illustrated embodiment has three such webs but there could be fewer or more than three. Gaps or openings are formed between the webs to allow for passage of smoke, etc. into and through the vent tube. The illustrated tube is formed with a longitudinal groove 188, the rear end of which is clearly visible in FIG. 8. This groove extends a substantial portion of the length of the vent tube and its purpose is explained hereinafter. Its front end at 191 acts as a stop to limit forward movement of the electrode as explained below. A rear stop member 193 can be mounted in a slot near the rear end of the groove to prevent the electrode from exiting the rear end of the tube.

A tapering slot 190 is formed on a rear end section of the tube as shown in FIGS. 5 and 8. The slot has a rounded forward end at 192. The function of this slot is to accommodate passage of the insulated wire 72 that is connected to the electrode tool. The slot allows the wire to pass upwardly for connection to the circuit board at illustrated in FIG. 4 and prevents the tube from interfering with the wire, particularly when the tube is moved rearwardly. Also the tube is formed with a downwardly projecting rib 194 that is parallel to and below the aforementioned groove 188. This rib can slide along a matching groove (not shown) formed along the bottom of the body portion 12 and this engagement both prevents rotation of the tube relative to the body portion and also limits outward movement of the vent tube when the front end of the rib meets the front end of the groove.

The rear end of the electrode tool 54 is supported in the tube by an electrode support member 200 shown separately in FIGS. 9 to 11 and shown mounted on the rear end of the electrode tool in FIG. 4. The exemplary support member has a tubular body 202 having a passageway 204 formed therein and extending the length of the tubular body. The tubular body can slide over the rear end section of the electrode and it is rigidly attached to the electrode via a metal connecting sleeve, such as the version 218 shown in FIGS. 12 and 13 (described below) so that it is slidable therewith and will not rotate on the electrode. The support member 200 has radially projecting arms 206,208 and 210 which extend at an acute angle to the longitudinal central axis of the tubular body. The arms are angled rearwardly towards the rear end 212 of the tubular body. The arm engages an interior surface 214 of the vent tube in a manner causing a friction fit between the ends of the arms and the interior surface. The exemplary support member 200 is made of an electrically insulating plastic and this plastic is chosen so that the three arms are somewhat resilient or bendable. This way the arms are made to press against the interior surface of the tube. The result is that the electrode tool normally maintains a selected position in the longitudinal direction thereof relevant to the vent tube. In order words the friction between the ends of the arms and the vent tube must be overcome by the user of the pencil in order to slide the electrode tool relative to the vent tube. Although only three arms are shown in the Figures, it is possible for the support member to have more than three arms but the gaps between the arms must be sufficient to allow for proper flow of smoke and fluids through the vent tube.

The exemplary support member 200 has an arm 210 that projects rearwardly and outwardly a greater distance than the other two arms because the arm 210 is constructed to slide along the aforementioned groove 188 in the vent tube. The engagement between the arm 210 and the groove prevents rotation of the electrode about a central longitudinal axis of the vent tube. This can be desirable, particularly if the outer end section of the electrode is not circular, for example if it is blade shaped and the blade is to be maintained in a certain orientation.

FIGS. 12 and 13 illustrate one form of a metal connecting sleeve 218 which can be used to connect the aforementioned insulated wire 72 to the rear end of the electrode tool. The sleeve 218 is made of a metal conductor such as brass and can be formed from a single sheet of thin metal. The sleeve has a tubular body 220 forming a passageway 222 sized to snuggly receive a rear end section of the electrode. Formed in two opposite sides of the tubular body are two spring arms 224,226 which are formed to extend slightly into the passageway. The wire 72 is connected to the rear end section 232 of the connecting sleeve. The end of the sleeve opposite the tab can be flared at 232 for relatively easy insertion of the electrode into the rear end of the sleeve. The U-shaped section 232 is formed so as to be pressed around and clamped to the end of the wire 72. This section has two bendable parallel arms, 234,236. The rear section of the electrode is formed with two flat indentations on opposite sides of the electrode (not shown). The rear section of the electrode is inserted into the connecting sleeve until the arms 224,226 engage their respective flat surfaces of the electrode, thereby holding the connecting sleeve and surrounding support member 200 securely in place.

Figure 16:
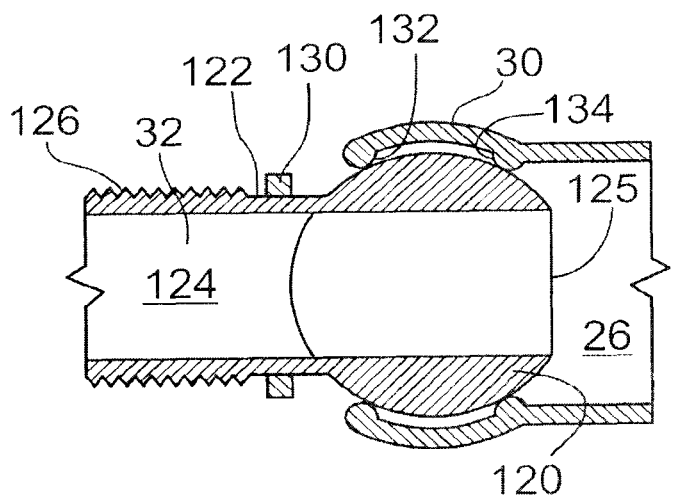
FIG. 16 is a cross sectional detail showing a ball joint for connecting a rear end socket section of the pencil to flexible tubing.

Reference will now be made to FIG. 16 which shows details of the ball socket 30 and the ball-swivel member 32 which can pivot in the ball socket. The ball-swivel member 32 has a ball portion 120 integrally connected to a tubular section 122. A straight internal passage 124 extends the length of the ball-swivel member 32 and this passage has an inner end at 125 which is always open to the airflow vent 26 formed in the main body portion 14. Annular ridges 126 can be formed on the tubular section in order to engage and hold an end section of flexible tubing such as ⅜ inch plastic tubing (not shown). Provided on the exterior of the tubular section or nipple 122 is an outwardly projecting annular ridge 130 which acts as a stop for the end of the plastic hose. The ball socket 30 can be provided with two annular ridges 132,134 which project inwardly so as to engage the spherical surface of the ball portion 120. These ridges help to seal the joint between the ball portion and the ball socket 30 as well as facilitate the pivoting motion of the ball portion in the socket.

In one exemplary embodiment of the present pencil 10, the passage 124 in the member 32 has a diameter of 0.32 inch while the ball portion 120 has an external diameter of 0.5 inch. This ball connection enables great flexibility in maneuvering the pencil 10 during an operation which can be important when carrying out a delicate operation.

Figure 17:
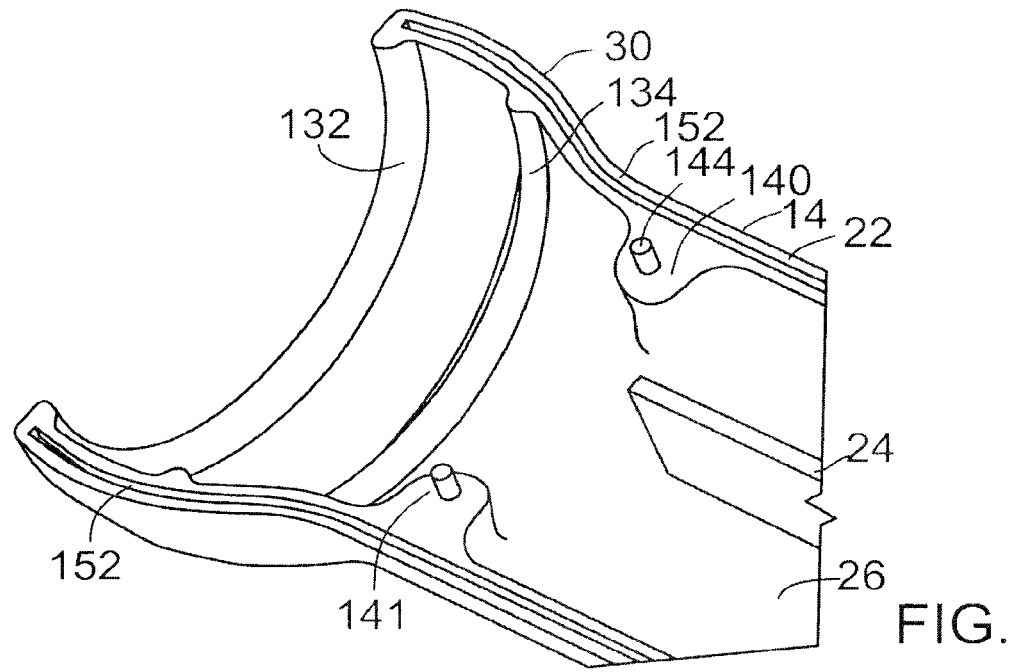
FIG. 17 is a detail view in perspective of one-half of the socket section formed at the rear end of the main body portion.
Figure 18:
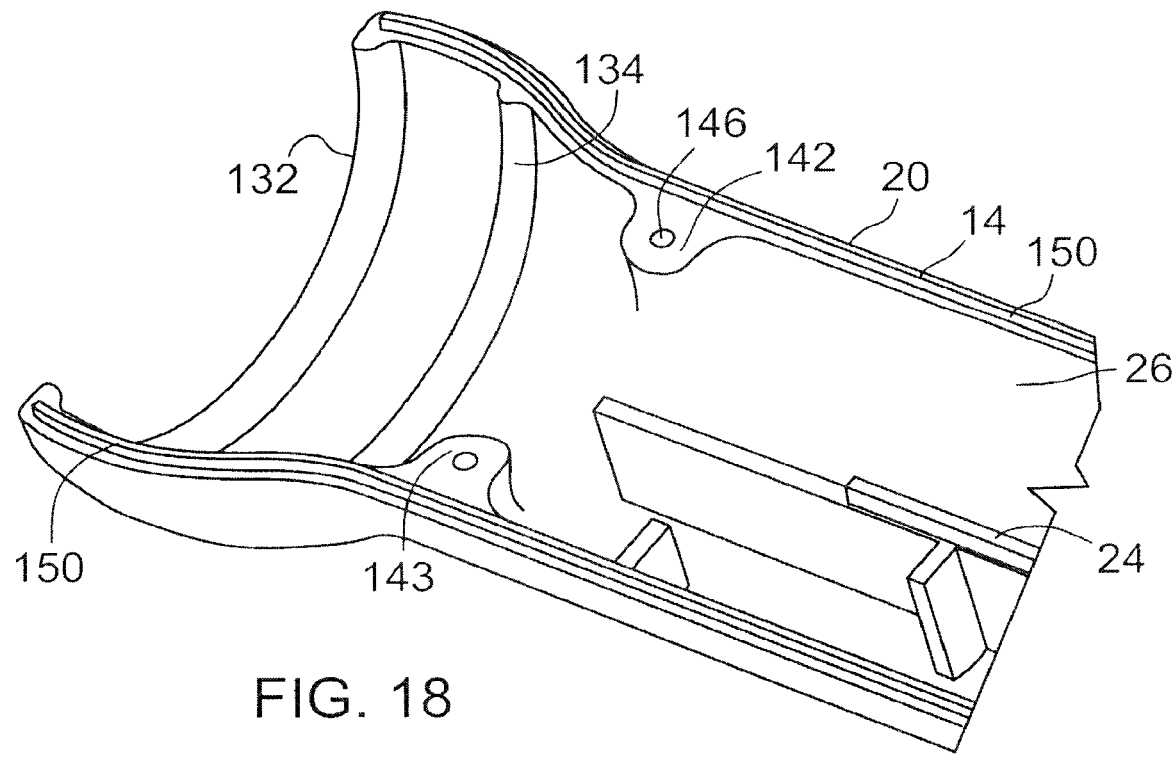
FIG. 18 is a detail view in perspective of the other half of a socket section at the rear end of the main body portion.

FIGS. 17 and 18 illustrate how the two ridges 132,134 are formed by two semi-annular sections, one section on each of the half-sections 20, 22. Also illustrated in these views are integral support formations 140-143 located close to the ball socket. From the two formations 140,141 extend respective plastic pins 144 which can be integrally formed with the half section. Corresponding pin receiving holes 146 are formed in support formations 142 and 143. When the two half-sections are placed together to form the main body portion, the pins 144 extend into the two holes 146 and can be ultrasonically welded in the holes. In addition to this connection there is a tongue and groove connection between the two half sections 20, 22. Tongues 150 can be formed along opposite side edges of the half section 20 while a corresponding, matching groove 152 can be formed along opposite side edges of the half section 22. The tongues 150 are permanently secured in the grooves by the ultrasonic welding operation or by adhesive.

As noted, both the longitudinal position of the electrode tool and that of the vent tube 12 are independently adjustable. It is generally understood that for best evacuation of smoke from an operating site, the front end of the vent tube 12 should be within ½ inch of the operating end portion of the tool. This preferred relative position can be obtained with the present pencil 10. As indicated above, insulating plastic material extends for most of the length of the blade but the front end section is exposed for the coagulation of blood vessels.

Under some circumstances, a surgeon may wish to withdraw the vent tube further away from the exposed front end section of the electrode blade in order, for example, to provide greater visibility of this front end section.

One construction for providing a friction mechanism to hold the vent tube in place is illustrated in FIGS. 3, 4 and 22. This construction involves the use of a rubber or rubberlike friction member 170 mounted in a chamber of the body portion 14 formed by internal transverse walls 36 and 38, in the body of FIGS. 3 and 4 and by transverse walls 39,41 in the body of FIG. 22. This chamber, which holds the friction member, is open towards the vent tube so that the inner side of the friction member engages the side of the vent tube. In an exemplary version, the inner side of the friction member is formed as a concave surface with a curvature corresponding to the exterior of the vent tube. The vent tube will generally hold the position to which it is pulled or pushed by the user. In an alternate construction, an O-ring is mounted around the vent for providing the friction mechanism.

FIGS. 19, 22 and 23 illustrate a second embodiment of an electrosurgical pencil 10' constructed in accordance with the application. FIGS. 20 and 21 illustrate an elongate vent tube 12' for use in the pencil 10'. This pencil also has a main body portion 14 similar to that in the first embodiment described above. The pencil 10' is similar to the electrosurgical pencil 10 except for the differences noted hereinafter with respect to its construction and its method of operation.

In the second embodiment 10' the illustrated wire 72 which is connected to the electrode tool is connected to same by means of a spring clip 74 which is shown separately in FIG. 24. The spring clip shown in FIG. 24 is formed with a passage 76 through which a rear end section of the electrode tool of the second embodiment of the pencil extends.

The spring clip is made of a suitable electrically conductive metal so as to transfer the electrical current from the wire 72 to the electrode tool. Arranged at one end of the spring clip is a wire clamp 78 for securing the end of the wire 72. Arranged on top of the spring clip is a ratchet engaging member 80 having a concave top surface 82 for engaging bumps on a ratchet formation 84 on the exterior of the rear section of the vent tube 12' (see FIGS. 19, 20 and 22). It will be understood that the manner in which the electrode tool is mounted in the vent tube allows its longitudinal position relative to the vent tube to be adjusted as desired by the user. The ratchet engaging member 80 and the ratchet formation 84 together form a ratchet mechanism for limiting and preventing unwanted sliding movement of the electrode tool 54 relative to the vent tube 12' of the second embodiment.

Figure 26:
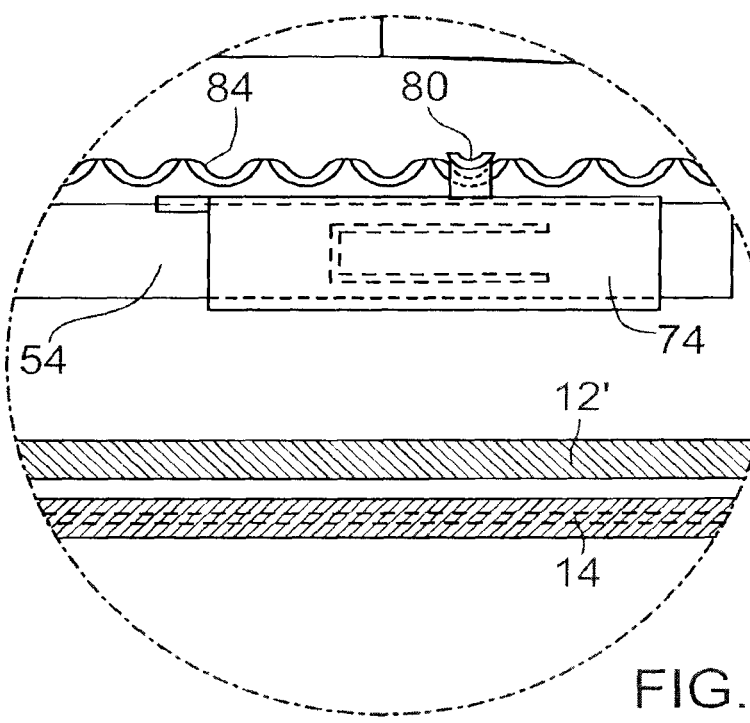
FIG. 26 is a detail elevation showing how ratchet teeth on one form of the vent tube are engaged by the spring clip attachment on the blade.
Figure 27:
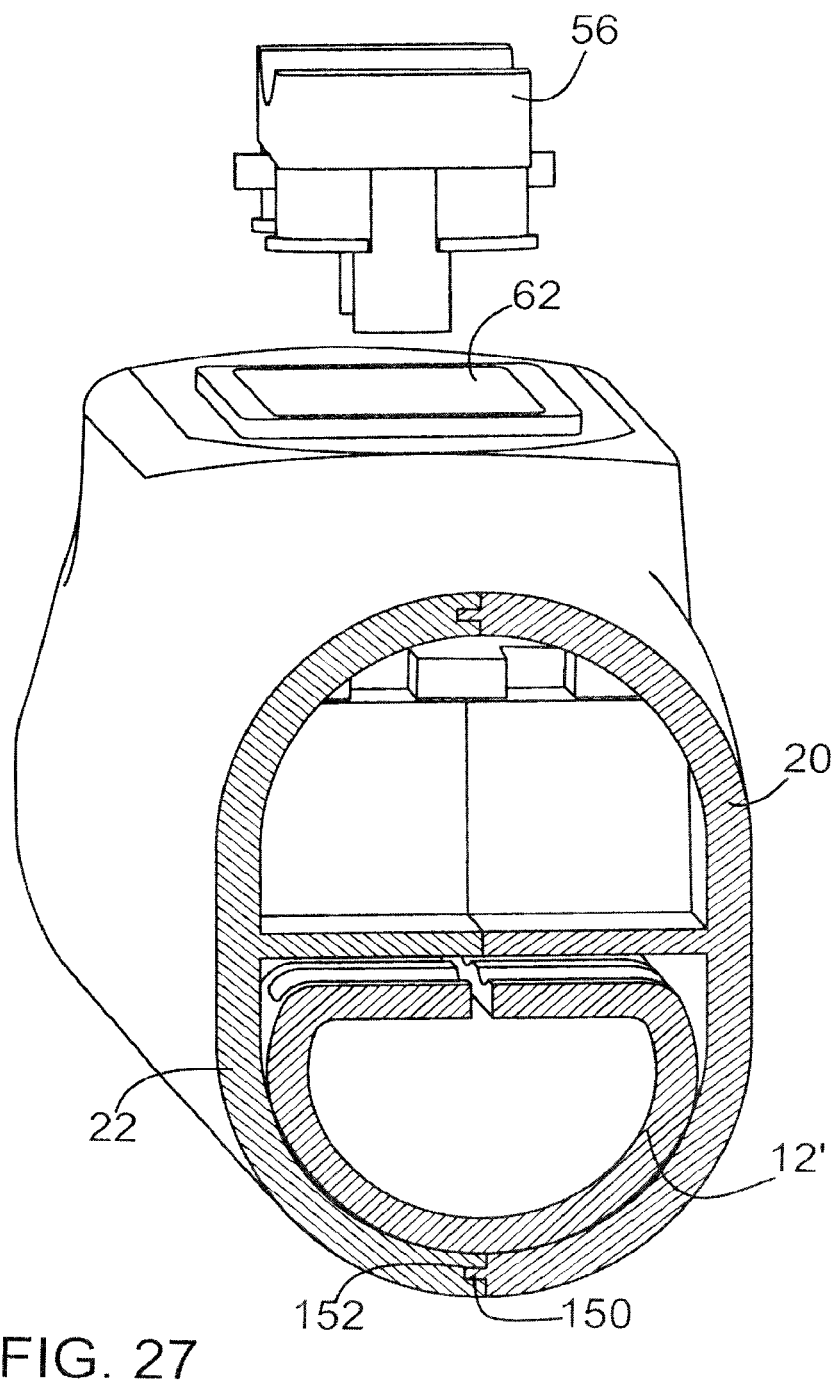
FIG. 27 is a transverse cross section of the pencil of FIG. 19, this view being taken along the line XXVII-XXVII of FIG. 19.

The vent tube 12' used in the pencil 10' will now be described with particular reference to FIGS. 20 to 23. The illustrated vent tube, which preferably is made of transparent plastic, has an open front end at 90' and an open rear end at 92'. The tube has a front section 94 with a circular transverse cross section and a rear section 96 which has a rounded exterior except for a substantially flat top portion 98. Extending at least most of the length of the top portion 98 is a central longitudinal slot 100 visible in FIG. 21. Located near the front end 90' of the tube is an eyelet guide 102 having a circular hole through which the electrode tool extends as illustrated in FIG. 22. It will be understood that the eyelet guide 102 provides support for a forward portion of the electrode tool while the rear end of the electrode tool is supported by means of the spring clip 74. As known in the art, the electrode tool is covered by an insulating plastic along a substantial central portion of its length (see FIG. 29). This insulating cover can extend through the guide 102. In order for the spring clip to provide support, a narrow section of the ratchet engaging member 80 extends through the slot 100 as shown in FIG. 26. The top section of the member 80 is wider than its bottom section and wider than the width of the slot 100. This arrangement provides a slidable support for the rear end of the electrode tool which is not covered by insulating plastic. The wider upper portion of the member 80 engages the ratchet formation 84 formed on the top of the top portion 98 of the vent tube and thus acts to prevent unwanted sliding movement of the blade while still allowing relative movement between the blade and the tube.

Instead of using the rubber friction member 170 described above, a suitable O-ring (not shown) can be mounted between the outer surface of the vent tube 12' along a rear portion of the front section 94 and the wall of the airflow vent 26 in order to provide both a seal around the vent tube and a friction fit that prevents unwanted relative movement between the vent tube and the main body portion 14. Alternatively there can be a close, friction fit between the vent tube and the airflow passage through which it extends so that the vent tube will not move relative to the main body portion unless manually pulled or pushed by the user.

An optional feature which can be included in either electrosurgical pencil described above is a lighting device to enable the surgeon or other user of the pencil to better see the operating site. Two possible alternatives for providing this lighting are illustrated in FIG. 22, the first being the use of one or more LED lights 160 mounted at the electrode end of the main body portion above the vent tube. The light or lights are connected to a small standard battery 162 located in a forward chamber 164 of the body portion 14. A standard electrical switch (not shown) can be used to close the circuit between the battery and the LED light 160.

As an alternate to the aforementioned lighting arrangement, a ring of LED lights 166 can be mounted at the open rear end of the vent tube in a manner so that the lights do not interfere with airflow through the vent tube or with the passage of the wire 72 into the vent tube. The array or ring of lights at 166 can be powered by the battery 162 through a suitable wire connection (not shown) or they can be powered by the same electrical source as the circuit board with this power being received through the wire 72 or a branch thereof. If the vent tube is made of clear transparent plastic, the light from the lights 166 will be transmitted down the vent tube to the surgical site.

Figure 28:
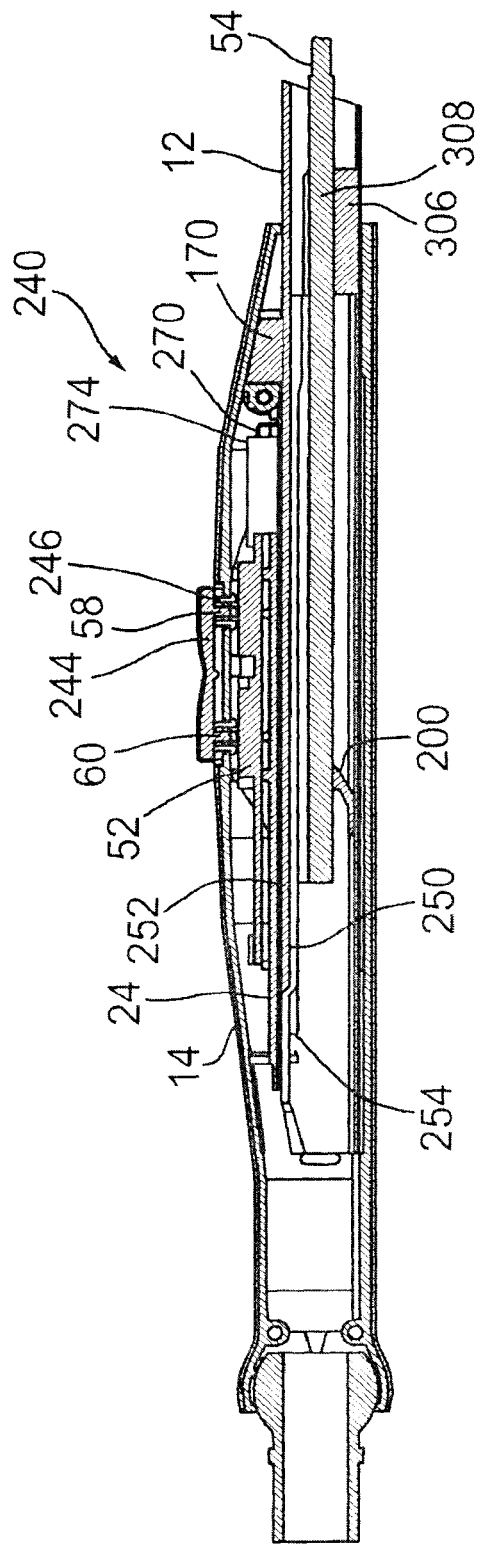
FIG. 28 is a longitudinal cross-section similar to FIG. 4 but showing a third embodiment of an electrosurgical pencil.
Figure 29:
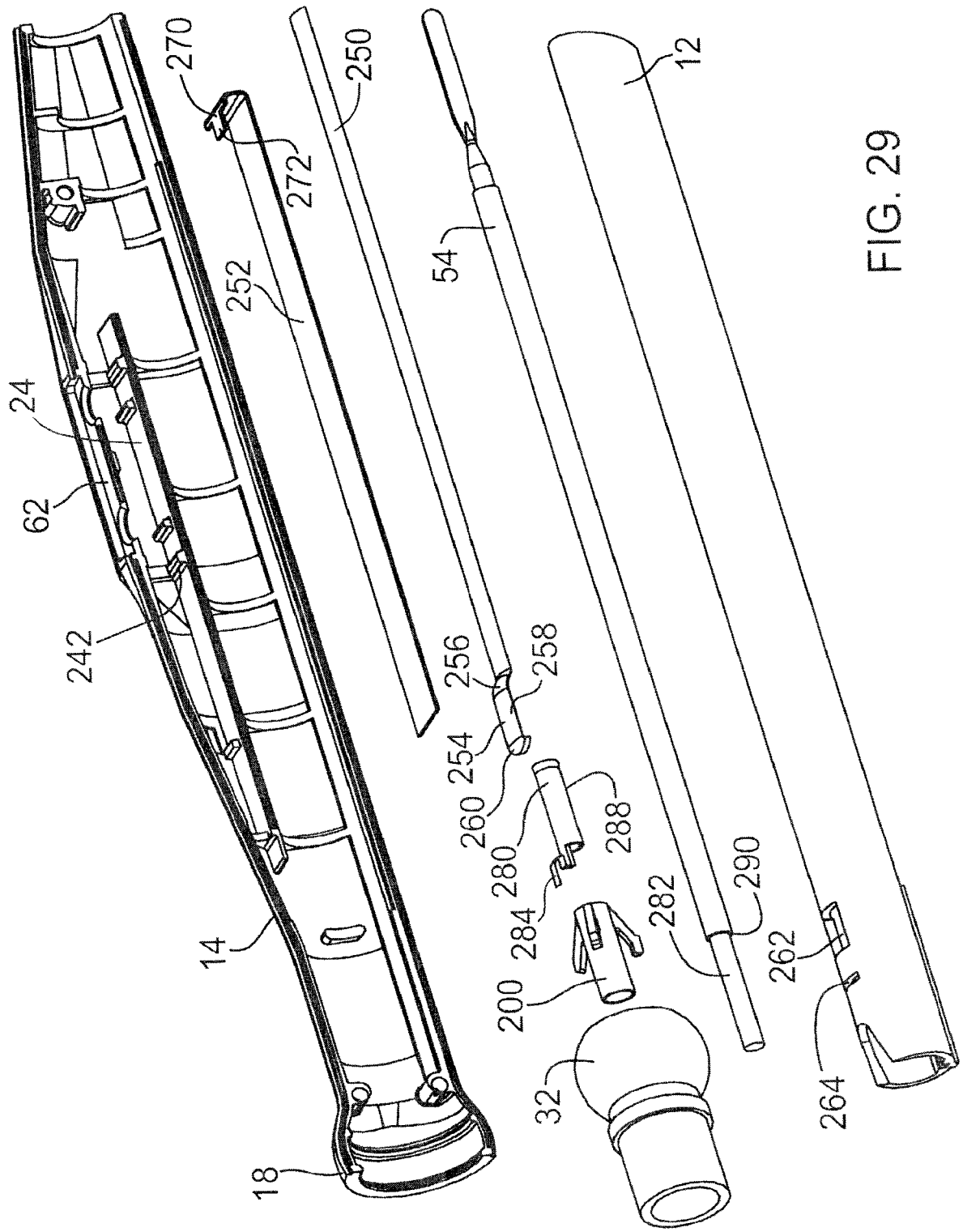
FIG. 29 is an exploded view of the pencil of FIG. 28, this view omitting a right half of the main body, the circuit board and the control switch.

FIGS. 28 and 29 illustrate a third embodiment of an electrosurgical pencil 240. The construction and operation of this pencil 240 is similar to the pencil 10 illustrated in FIGS. 1 to 4 except for the differences noted and described hereinafter. This pencil has a main body portion 14 forming a handle grippable by a user, only one half of which is shown in the exploded view of FIG. 29. The main body portion has an internal longitudinal wall structure 24 similar to that in the first embodiment. However, formed on the upper surface of this wall structure are a series of transverse ridges 242 on which is mounted the circuit board 52, which is shown separately in FIG. 31. An alternate form of electrical switch mechanism 244 is mounted on the main body portion in a manner that allows it to be used to operate the circuit board. As with the switch mechanism 56, the switch mechanism 244 is also a rocker switch and is shown separately in FIG. 30. This switch mechanism also has two downwardly projecting pins 58, 60 which project through two holes formed in the recessed section 62 of the main body portion. In the switch mechanism 56 of the first pencil embodiment, the mechanism is connected to the main body of the pencil by two flexible clip mechanisms 56, 59 illustrated clearly in FIG. 14. Each of the clip mechanisms comprises two spaced apart arc-shaped clip members 61, 63. Each of these members is formed with a bottom edge having an outwardly projecting flange 65. Because of the flexibility of the clip members, it is possible to push these through the round holes 64, 66 in order to attach the switch 56 to the main body portion. It will be understood that the external diameter of the two cooperating edge flanges exceeds the diameter of their respective hole, 64, 66 so that when these flanges pass through the hole, they will retain the switch in place.

Figure 30:
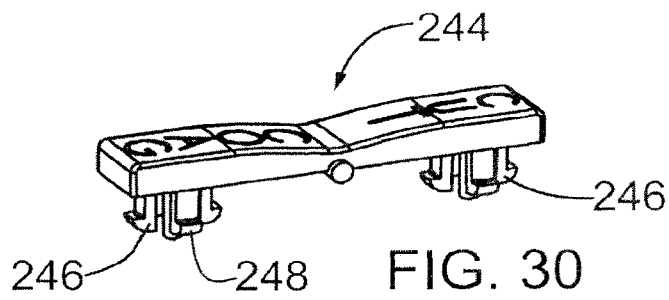
FIG. 30 is a perspective view taken from above illustrating the electrical control switch used in third embodiment.
Figure 31:
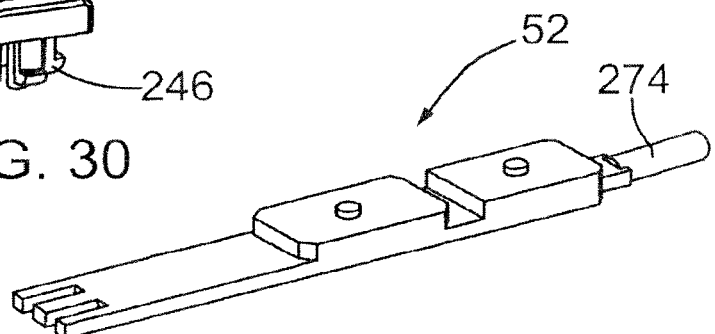
FIG. 31 is a perspective view taken from above showing the circuit board used in the third embodiments of the pencil.
Figure 33:
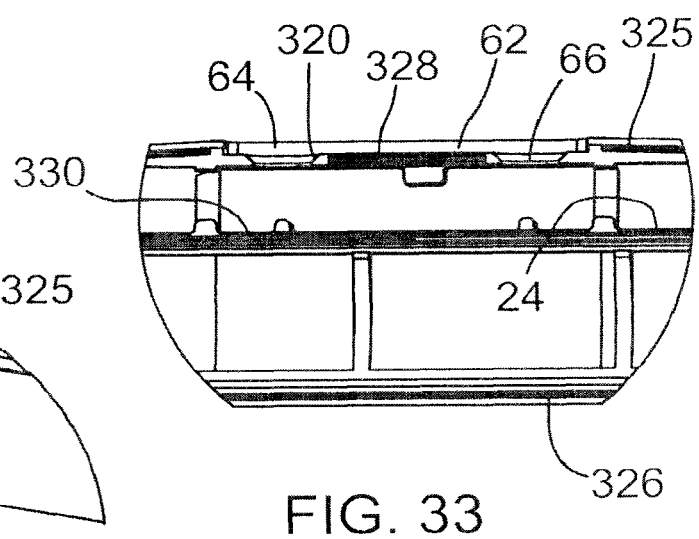
FIG. 33 is a detail view showing a central section of a left half of the main body portion of the pencil.

The switch mechanism 244 shown in FIGS. 28 and 30 is of similar construction except that instead of only two clip members for each clip mechanism, there are four similar clip members 246 distributed evenly about the projecting pin 58, 60. Again each clip member is formed with an outwardly projecting bottom flange 248 and the four bottom flanges of each clip mechanism will cooperate together to hold their respective end of the switch in place on the body portion of the pencil. As shown in FIG. 33 the edge of each hole 64,66 preferably has a lead-in chamfer 320 to facilitate insertion of the clip members through the holes.

It will be understood that the circuit board 52 is connected to a power source by insulated wire 70 (not shown in FIGS. 28 and 29) similar to the wire 70 shown in FIGS. 3 and 4. However, the conducting arrangement for providing electrical power to the electrode tool is different in the pencil 240. In this pencil, there is a first metal conducting strip 250 which is mounted in the vent tube 12 and is in electrical contact with the electrode tool 54 in any of a plurality of extended positions. In addition, there is a second metal conducting strip 252 which is mounted in the main body portion 14 directly below the wall structure 24 and adjacent to the vent tube. The two metal conducting strips are in sliding electrical contact with one another and the second metal conducting strip 252 is adapted to electrically connect the first metal conducting strip 250 to the electrical control provided by the circuit board.

Figure 35:
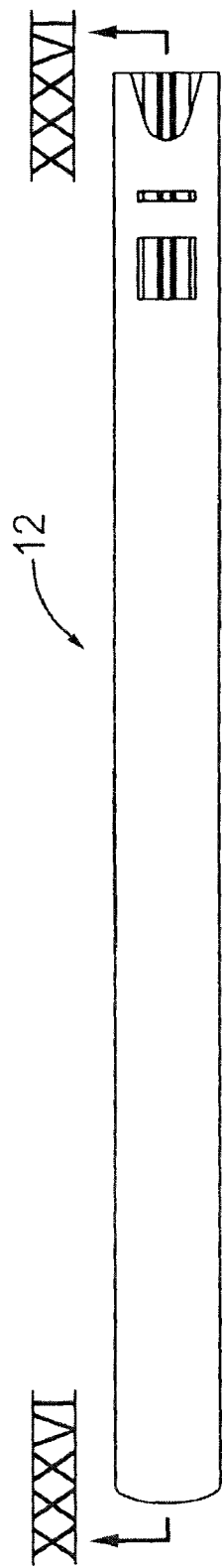
FIG. 35 is a top view of the vent tube shown in FIG. 29.
Figure 36:
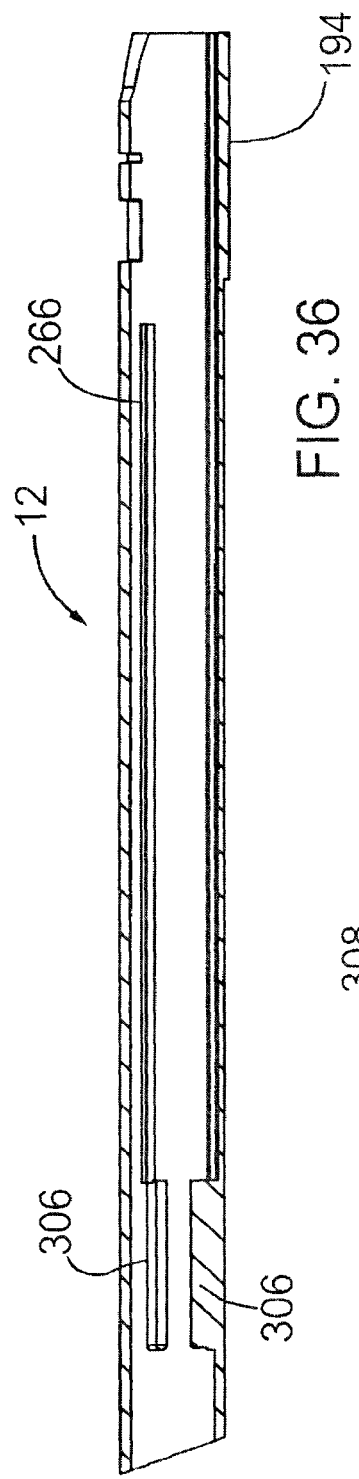
FIG. 36 is a longitudinal cross-section of the vent tube taken along the line XXXVI-XXXVI of FIG. 35.

The exemplary conducting strip 250 illustrated in FIG. 29 has an upward projecting end section 254. The strip 250 bends upwardly at 256 and then bends rearward to form a short flat section 258, which extends generally parallel to the main body of the conducting strip 250. The end section also has a downwardly extending end flange at 260. The vent tube 12 as shown in FIGS. 29, 35 and 36 is modified to accommodate the conducting strip 250. In particular, it is formed with a rectangular opening 262 on its top side. The opening 262 is formed in a rear end section of the vent tube 12. The upwardly bent rear end section 254 is sized to fit through the opening 262 and to project there from so as to slidingly engage the second metal conducting strip 252 as shown in FIG. 28. The end flange 260 is pushed into a transverse slot 264 also formed on the top side of the vent tube. The flange engagement holds the strip 252 in place, preventing longitudinal movement of the strip.

In addition, in order to hold the conducting strip 250 in place, the vent tube 12 of the third embodiment is formed internally with two longitudinal, spaced-apart rib-like connectors, 266, 268 that extend at least a major portion of the length of the vent tube as shown in FIG. 36. These rib-like connectors capture the longitudinal edges of the conducing strip 250. It will also be appreciated that instead of a relatively flat conducting strip 250, this first conducting member can be constructed differently, for example in the form of an elongate metal conducting member such as a suitable conducting wire having a round cross section. Such a wire can be captured in a single slot formed on the upper side of the tube. The exemplary second metal conducting strip 252 is formed with a bent back end section 270. As illustrated in FIG. 28, the end section 270 extends around the forward end of the wall structure 24. The end section 270 can be formed with a relatively narrow, rearwardly projecting tongue 272 which projects into the sleeve of an electrical connector 274 mounted on the forward end of the circuit board 52 (see FIG. 31). In this way power from the circuit board is provided to the second conducting strip 252 which is then able to transmit this power to the first conducting strip 250 whatever extended position of the vent tube 12 is selected. The two strips 250,252 can be made of brass.

Figure 32:
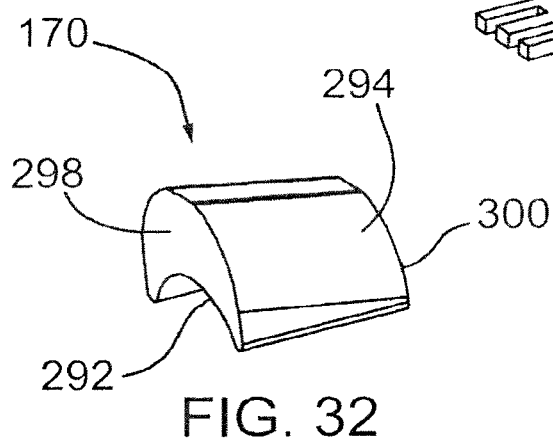
FIG. 32 is a perspective view taken from above and from the rear showing the rubber pad used in the ESU pencil of FIG. 28.

A different form of metal connector that acts as an electrical conductor is used in the ESU pencil 240 as compared to the metal connecting sleeve 218 shown in FIGS. 12 and 13 and described above. In particular, a metal connector 280 is mounted on the bare, electrically conducting, rear section 282 of the electrode tool. The connector 280 has a bent metal conducting tongue 284 that extends from the metal connector to the first metal conducting strip 250 to provide an electrical connection slidable along this conducting strip 250. The main portion of the metal connector 280 is in the form of a split sleeve 288 able to expand sufficiently to fit snugly on the rear conducting section 282 of the electrode tool. The bent conducting tongue 284 is formed initially as a straight, elongate tongue projecting rearwardly. In this form the conductor is telescoped over the rear section 282. Then the electrode support member 200 is pushed over the split sleeve 285 until it rests against the shoulder 290 formed on the electrode by its plastic covering. In this way the support member 200 holds the connector 280 firmly in place on the rear section of the electrode. The rearwardly projecting tongue of the connector can then be bent in the forwards direction and then rearwards to form a spring-like contact that can slide along the adjacent surface of the conducting strip 250. FIG. 32 illustrates an exemplary form of the above described rubber friction member 170. This friction member is mounted in the main body portion 14 near the forward end as shown in FIG. 28. It has an inner surface at 292 in the form of a cylindrical arc having a radius corresponding to the external radius of the vent tube. This inner surface engages the upper side of the vent tube and presses against same in order to restrict the sliding movement of the vent tube in its passageway. An upper surface 294 of the friction member or pad can also be curved and this surface tapers from the rear end 298 to the front end 300 so that the pad can fit within the tapered front section of the main body of the pencil.

Figure 37:
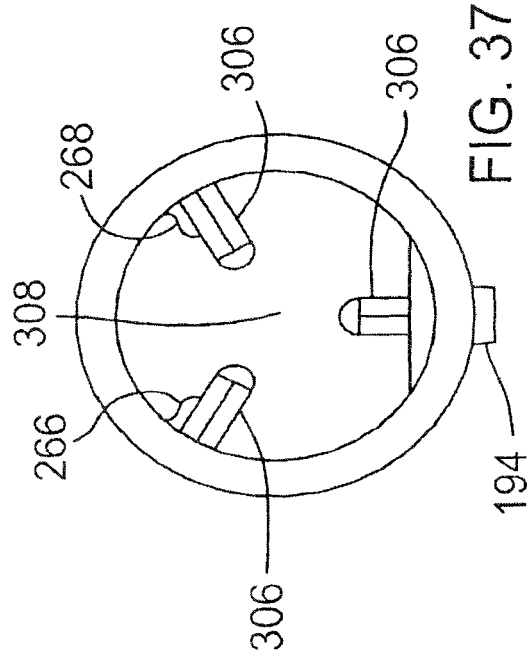
FIG. 37 is a front end view of the vent tube of FIG. 35.

The support for the forward section of the electrode tool 54 also differs in the third version of the ESU pencil compared to the first embodiment of the pencil. Instead of the support arrangement shown in FIG. 7 having the cylindrical section 184, there are formed in the forward section of the vent tube a plurality of longitudinal guide ribs 306. As shown in FIGS. 36 and 37, there are three such guide ribs distributed evenly about the circumference of the vent tube, that is, at angles of about 120 degrees to one another. The electrode or electrode tool extends through a central passage 308 defined by the guide ribs and is slidably supported by these guide ribs.

Figure 34:
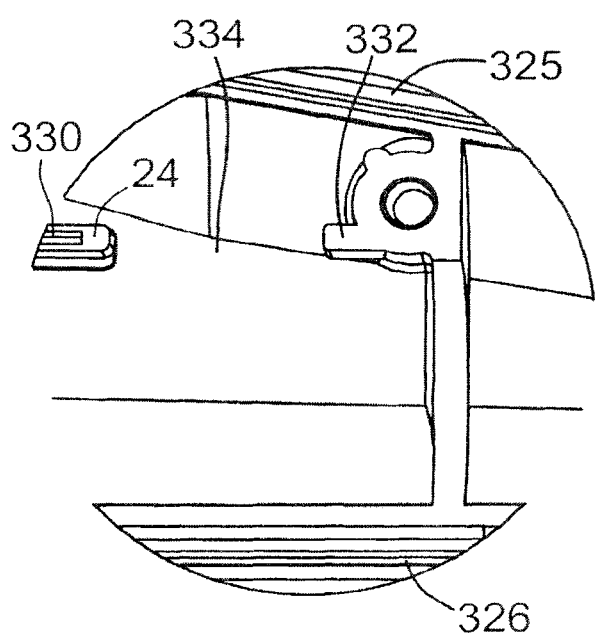
FIG. 34 is a detail view of forward section of the left half of the main body portion.

FIGS. 33 and 34 also illustrate an exemplary feature for attaching the two half sections of the main body portion 14 to each other. In particular weld beads can be provided at 325,326 along top and bottom edges of one half of the main body portion. A further short weld bead can be provided at 328 along the top edge that extends between holes 64,66. A further weld bead can be provided at 330 along one half of the internal wall structure 24. These weld beads fit into corresponding grooves formed in the opposite half of the main body portion.

There is also shown in FIG. 34 one half of a projecting stop 332 that, together with the wall structure 24 forms a gap 334. Through this gap the bent end section 270 of the second metal conducting strip 252 extends in the assembled condition of the pencil. The stop 332 prevents any forward movement of the conducting strip 252 in its passageway.

While the present application has been illustrated and described as embodied in exemplary embodiments, e.g. embodiments having particular utility in surgical applications, it is to be understood that the present application is not limited to the details shown herein, since it will be understood that various omissions, modifications, substitutions and changes in the forms and details of the disclosed electrosurgical pencils and their operation may be made by those skilled in the art without departing in any way from the scope of the present application. For example, those of ordinary skill in the art will readily adapt the present disclosure for various other applications without departing from the scope of the present application.

What is claimed is:

1. An electrosurgical tool for performing a surgical procedure, comprising:
   an elongated body;
   an elongated vent tube mounted in the body and configured to move longitudinally relative to the body;
   an elongated electrode mounted in the vent tube and configured to move longitudinally relative to at least one of the vent tube or the body;
   a conducting member disposed outside of the vent tube and in the body; and
   a connector electrically coupled to the electrode and is axially fixed to the vent tube, the connector in sliding contact with the conducting member, such that the electrode and the conducting member are slidably, electrically connected to one another and the connector moves longitudinally with the vent tube.

2. The electrosurgical tool according to claim 1, wherein the electrode is configured to move longitudinally relative to both the vent tube and the body.

3. The electrosurgical tool according to claim 1, wherein the electrode has a proximal end section, the connector electrically coupled to the electrode.

4. The electrosurgical tool according to claim 1, wherein the connector has a bent conducting tongue in sliding contact with the conducting member.

5. The electrosurgical tool according to claim 1, further comprising a circuit board for controlling electrical operation of the electrode, the circuit board mounted in the body and connectable to a power source.

6. The electrosurgical tool according to claim 5, further comprising an electrical connector mounted to the circuit board and electrically connected to the electrode via the conducting member and the connector.

7. The electrosurgical tool according to claim 1, wherein the conducting member is axially fixed relative to the vent tube.

8. The electrosurgical tool according to claim 1, wherein the vent tube has a proximal end section defining an opening in a top side thereof, the conducting member having an upwardly bent proximal end section extending into the opening.

9. An electrosurgical tool for performing a surgical procedure, comprising:
   a main body;
   an elongated vent tube disposed in the main body, the vent tube having a wall that defines an opening through a thickness thereof;
   an elongated electrode disposed in the vent tube and configured to move longitudinally relative to at least one of the main body or the vent tube;
   a first conducting member electrically coupled to the electrode and restrained within the vent tube; and
   a second conducting member disposed outside of the vent tube and within the main body, wherein the first conducting member has a section that extends through the opening of the vent tube and into sliding contact with the second conducting member.

10. The electrosurgical tool according to claim 9, wherein the electrode is configured to move longitudinally relative to both the vent tube and the main body.

11. The electrosurgical tool according to claim 9, wherein the vent tube is configured to slide relative to and within the main body.

12. The electrosurgical tool according to claim 9, wherein the wall of the vent tube has an outer surface, and an inner surface defining a longitudinally-extending passageway, the opening of the wall of the vent tube extending through the inner and outer surfaces of the vent tube.

13. The electrosurgical tool according to claim 12, wherein the electrode is mounted in the passageway of the vent tube.

14. The electrosurgical tool according to claim 9, wherein the section of the first conducting member is bent upwardly.

15. The electrosurgical tool according to claim 9, further comprising longitudinal guide ribs mounted in the vent tube adjacent a distal end section of the vent tube.

16. The electrosurgical tool according to claim 15, wherein the longitudinal guide ribs are circumferentially disposed on an internal surface of the vent tube.

17. An electrosurgical tool for performing a surgical procedure, comprising:
   a main body;
   an elongated vent tube disposed in the main body, the vent tube having a wall that defines an opening through a thickness thereof;
   an elongated electrode disposed in the vent tube and configured to move longitudinally relative to at least one of the main body or the vent tube;
   a first conducting member electrically coupled to the electrode; and
   a second conducting member, wherein the first conducting member has a section that extends through the opening of the vent tube and into sliding contact with the second conducting member, wherein the first conducting member is axially fixed to the vent tube, such that the first conducting member moves longitudinally with the vent tube.

* * * * *